US011225642B2

(12) United States Patent
Osafune et al.

(10) Patent No.: US 11,225,642 B2
(45) Date of Patent: Jan. 18, 2022

(54) METHOD FOR PRODUCING RENAL PROGENITOR CELLS

(71) Applicants: KYOTO UNIVERSITY, Kyoto (JP); ASTELLAS PHARMA INC., Tokyo (JP)

(72) Inventors: Kenji Osafune, Kyoto (JP); Takafumi Toyohara, Kyoto (JP); Yukiko Yamagishi, Tokyo (JP)

(73) Assignees: Kyoto University, Kyoto (JP); Astellas Pharma Inc., Tokyo (JP)

( * ) Notice: Subject to any disclaimer, the term of this patent is extended or adjusted under 35 U.S.C. 154(b) by 439 days.

(21) Appl. No.: 14/897,319

(22) PCT Filed: Jun. 11, 2014

(86) PCT No.: PCT/JP2014/066081
§ 371 (c)(1),
(2) Date: Apr. 8, 2016

(87) PCT Pub. No.: WO2014/200115
PCT Pub. Date: Dec. 18, 2014

(65) Prior Publication Data
US 2016/0137985 A1 May 19, 2016

(30) Foreign Application Priority Data

Jun. 11, 2013 (JP) .............................. JP2013-123072
Apr. 25, 2014 (JP) .............................. JP2014-092108

(51) Int. Cl.
*A61K 35/22* (2015.01)
*C12N 5/071* (2010.01)
*A61K 38/18* (2006.01)
*A61K 35/545* (2015.01)

(52) U.S. Cl.
CPC ............ *C12N 5/0687* (2013.01); *A61K 35/22* (2013.01); *A61K 38/1841* (2013.01); *C12N 5/0686* (2013.01); *A61K 35/545* (2013.01); *C12N 2501/15* (2013.01); *C12N 2501/155* (2013.01); *C12N 2501/999* (2013.01); *C12N 2506/45* (2013.01)

(58) Field of Classification Search
CPC .......................... G01N 33/5044; C12N 5/0619
See application file for complete search history.

(56) References Cited

U.S. PATENT DOCUMENTS

| | | | |
|---|---|---|---|
| 5,843,780 A | 12/1998 | Thomson | |
| 2007/0031966 A1 | 2/2007 | Dressier et al. | |
| 2009/0047263 A1 | 2/2009 | Yamanaka et al. | |
| 2010/0111908 A1 | 5/2010 | Lin et al. | |
| 2011/0311494 A1* | 12/2011 | Benjamin | C12N 5/0686 424/93.7 |
| 2011/0311495 A1 | 12/2011 | Dekel | |

FOREIGN PATENT DOCUMENTS

| | | | |
|---|---|---|---|
| WO | WO 2004/106499 A1 | 12/2004 | |
| WO | WO 2007/069666 A1 | 6/2007 | |
| WO | WO 2008/094597 A2 | 8/2008 | |
| WO | WO 2012/011610 A1 | 1/2012 | |
| WO | WO-2012011610 A1 * | 1/2012 | ......... G01N 33/5073 |
| WO | WO 2013/094771 A1 | 6/2013 | |

OTHER PUBLICATIONS

James et al (Developmental Biology, 288: 113-125, 2005) (Year: 2005).*
Mugford et al (Dev Biol, 324(1): 88-98, 2008) (Year: 2008).*
Borowiak et al (Cell Stem Cell. Apr. 3, 2009; 4(4): 348-358.) (Year: 2009).*
Fei et al (Science China Life Sciences, 53(4): 497-503, 2010) (Year: 2010).*
Mugford (Dev Biol, 324(1): 88-98, 2008 (Year: 2008).*
Toyohara (Translational Medicine 2015;4:980-992) (Year: 2015).*
Office Action, Written Opinion and Search Report dated Sep. 28, 2016, in Singapore Application No. 11201510201P.
International Preliminary Report on Patentability issued Dec. 15, 2015, Written Opinion of the International Searching Authority, dated Sep. 16, 2014.
Kester et al., "Expression of TGF-β Stimulated Clone-22 (TSC-22) in Mouse Development and TGF- β Signalling," Developmental Dynamics, 2000, 218:563-572.
Office Action dated Nov. 24, 2017, in TW 103120163, with English translation.
Supplementary European Search Report dated Jan. 20, 2017, in EP 14811223.8.
Dressler, Gregory R., "The Cellular Basis of Kidney Development," Annu. Rev. Cell. Dev. Biol., Nov. 1, 2006 (online Jul. 5, 2006), 22(1):509-529.
Osafune, Kenji, "In vitro regeneration of kidney from pluripotent stem cells," Experimental Cell Research, Oct. 1, 2010 (online May 6, 2010), 316(16):2571-2577.
Yu et al., "Dorsomorphin inhibits BMP signals required for embryogenesis and iron metabolism," Nature Chemical Biology, Jan. 1, 2008 (online Nov. 18, 2007), 4(1):33-41.
International Search Report dated Sep. 16, 2014, in PCT/JP2014/066081.
Araoka et al., "Efficient and Rapid Induction of Human iPSCs/ESCs into Nephrogenic Intermediate Mesoderm Using Small Molecule-Based Differentiation Methods," PLoS ONE, Jan. 2014, 9(1):e84881:1-14.
Batchelder et al., "Renal ontogeny in the rhesus monkey (*Macaca mulatta*) and directed differentiation of human embryonic stem cells towards kidney precursors," Differentiation, 2009, 78:45-56.

(Continued)

Primary Examiner — Anoop K Singh
Assistant Examiner — Magdalene K Sgagias
(74) Attorney, Agent, or Firm — Foley & Lardner LLP

(57) ABSTRACT

The present invention provides: a method for producing renal progenitor cells from intermediate mesoderm cells, which comprises a step of culturing intermediate mesoderm cells in a medium containing a TGFβ signaling activator(s) and a BMP inhibitor(s); the renal progenitor cells produced by the method; a pharmaceutical composition comprising the renal progenitor cells; and a therapeutic drug for kidney diseases comprising the renal progenitor cells.

19 Claims, 13 Drawing Sheets
Specification includes a Sequence Listing.

(56) References Cited

OTHER PUBLICATIONS

Kim et al., "Nephrogenic Factors Promote Differentiation of Mouse Embryonic Stem Cells into Renal Epithelia," J. Am. Soc. Nephrol., 2005, 16:3527-3534.
Kobayahsi et al., "Six2 Defines and Regulates a Multipotent Self-Renewing Nephron Progenitor Population throughout Mammalian Kidney Development," Cell Stem Cell, Aug. 7, 2008, 3:169-181.
Mae et al., "Combination of small molecules enhances differentiation of mouse embryonic stem cells into intermediate mesoderm through BMP7-positive cells," Biochemical and Biophysical Communications, 2010, 393:877-882.
Mae et al., "Monitoring and robust induction of nephrogenic intermediate mesoderm from human pluripotent stem cells," Nature Communications, Dec. 2, 2013, 4:1367, 11 pages.
Osafune et al., "Identification of multipotent progenitors in the embryonic mouse kidney by a novel colony-forming assay," Development, 2006, 133:151-161.
Osafune et al., "Kidney Regeneration and Disease Modeling Research using iPS Cell Technology," Japanese Society for Pediatric Nephrology, Apr. 15, 2013, 26(1):64-69, with partial English translation.
Office Action dated Mar. 30, 2018, in RU 2015156492, with English translation.
Office Action dated Aug. 28, 2018, in RU 2015156492, with English translation.
Bussolati et al., "Isolation of Renal Progenitor Cells from Adult Human Kidney," American Journal of Pathology, Feb. 2005, 166(2):545-555.
Hammerman, Marc R., "Transplantation of renal precursor cells: a new therapeutic approach," Pediatr. Nephrol., 2000, 14:513-517.
Verhovskaja et al., "The effect of alkoxy-substituted glycerol on the morphofunctional properties of a transplantable cell culture," Kriobiology, 1990, 30-33, with English abstract on p. 30.
Office Action dated Apr. 26, 2018, in CN 201480033367.1.
Krause et al., "Noggin," The International Journal of Biochemistry & Cell Biology, 2011, 43:478-481.
Mae et al., "Monitoring and robust induction of nephrogenic intermediate mesoderm from human pluripotent stem cells," Nature Communications, Jan. 22, 2013, 4:1367, 11 pages.
Office Action dated Feb. 26, 2020, in CA 2,915,085.

\* cited by examiner

A DMSO

B TGFβ1+Noggin

C TGFβ1+LDN193189

D TGFβ1+DMH1

E IDE1+Dorsomorphin

F IDE2+Dorsomorphin

G TGFβ2+LDN193189

H TGFβ3+LDN193189

METHOD FOR PRODUCING RENAL PROGENITOR CELLS

CROSS-REFERENCE TO RELATED APPLICATIONS

This application is a National Stage application of PCT/JP2014/066081, filed Jun. 11, 2014, which claims priority from Japanese application nos. JP 2013-123072, filed Jun. 11, 2013, and JP 2014-092108, filed Apr. 25, 2014.

TECHNICAL FIELD

The present invention relates to a method for inducing the differentiation of pluripotent stem cells into renal (or kidney) progenitor cells. The present invention also relates to a therapeutic drug for kidney diseases comprising the thus obtained renal progenitor cells.

BACKGROUND ART

The kidney is an important organ that has functions to maintain physical health by removing, through filtration, waste products, such as harmful or detrimental substances generated as a result of metabolic activities within living organisms, from bloods. An example of kidney diseases is renal failure, and an example of therapeutic methods therefor is dialysis. However, the burden imposed by medical expenses required for such therapy is high, and thus renal failure is still a world-wide problem, not only from medical perspective, but also from medical economic aspect. Another example of therapies for renal failure is renal transplantation, although shortage of donor organs is a serious issue of concern.

Meanwhile, pluripotent cells such as embryonic stem cells (ES cells) and induced pluripotent stem cells (iPS cells), which can be obtained via introduction of undifferentiated cell-specific genes into somatic cells, have been reported (Patent Documents 1 and 2). As a therapeutic method for renal failure, therefore, the therapy that involves transplanting renal cells obtained by inducing differentiation of these pluripotent stem cells has been investigated. Moreover, development of therapeutic drugs using homogeneous renal cells derived from these pluripotent stem cells is also under consideration.

The mammalian kidneys are generated through three stages of kidney development of pronephros, mesonephros and metanephros. Among these stages, the metanephros is known to be generated in the posterior region of the intermediate mesoderm. In this context, methods for inducing differentiation of mouse pluripotent stem cells into the intermediate mesoderm for the purpose of nephrogenesis have been studied (Non-Patent Document 1), and OSR1 was confirmed as a marker characteristic to the intermediate mesoderm. In addition, by study using human iPS cells ('OSR1-GFP reporter human iPS cells') into which a green fluorescent protein (GFP) gene had been introduced using a bacterial artificial chromosome (BAC) vector through homologous recombination with the endogenous OSR1 allele, induction of differentiation of human pluripotent stem cells into the intermediate mesoderm was successfully achieved by using Activin A, Wnt, BMP and a variety of low-molecular-weight compounds (Non-Patent Document 2 and Patent Document 3).

Considering transplantation into kidney tissues, it is preferable to induce renal progenitor cells at a more advanced stage of differentiation into a kidney than stage of the intermediate mesoderm. SIX2 is known as a factor that characterizes renal progenitor cells (Non-Patent Document 4). However, there is no established method for artificially inducing renal progenitor cells from intermediate mesoderm.

PRIOR ART DOCUMENT

Patent Document

Patent Document 1: U.S. Pat. No. 5,843,780
Patent Document 2: WO2007/069666
Patent Document 3: WO2012/011610

Non-Patent Document

Non-Patent Document 1: Mae S, et al. (2010), Biochem Biophys Res Commun. 393: 877-82
Non-Patent Document 2: Mae S, et al. (2013), Nat Commun. 4: 1367
Non-Patent Document 3: Osafune K, et al. (2006), Development. 133: 151-61
Non-Patent Document 4: Kobayashi A, et al. (2008), Cell Stem Cell. 3: 169-81

SUMMARY OF INVENTION

An object of the present invention is to provide a method for inducing differentiation of intermediate mesoderm cells into renal progenitor cells, more specifically to provide a method for inducing differentiation of intermediate mesoderm cells into renal progenitor cells comprising a step of inducing intermediate mesoderm cells, which are induced from pluripotent stem cells, into renal progenitor cells.

We have conducted concentrated studies in order to attain the above-mentioned object. As a result, we have now found, for the first time, that it is possible to induce differentiation of intermediate mesoderm cells into renal progenitor cells by culturing the intermediate mesoderm cells in a medium containing TGFβ signaling activator and BMP inhibitor. The present invention has been completed based on such finding.

Specifically, the present invention encompasses the following features.

[1] A method for producing renal progenitor cells from intermediate mesoderm cells, comprising the following step of: culturing intermediate mesoderm cells in a medium containing a TGFβ signaling activator (s) and a BMP inhibitor(s), thereby inducing renal progenitor cells from intermediate mesoderm cells.

[2] The method of [1], wherein the renal progenitor cells are SIX2-positive cells.

[3] The method of [1] or [2], wherein the intermediate mesoderm cells are OSR1-positive cells.

[4] The method of any one of [1] to [3], wherein the TGFβ signaling activator is one or more substances selected from the group consisting of TGFβ1, TGFβ2, TGFβ3, IDE1, and IDE2.

[5] The method of any one of [1] to [4], wherein the BMP inhibitor is one or more substances selected from the group consisting of Dorsomorphin, Noggin, LDN193189, and DMH1.

[6] The method of any one of [1] to [3], wherein the TGFβ signaling activator is TGFβ1, and the BMP inhibitor is DMH1.

[7] The method of any one of [1] to [6], wherein the intermediate mesoderm cells are intermediate mesoderm cells induced from pluripotent stem cells.

[8] The method of [7], wherein the intermediate mesoderm cells are intermediate mesoderm cells produced by a method comprising the following steps of:
    (i) culturing pluripotent stem cells in a medium containing one or more substances selected from the group consisting of Activin A, a GSK-3β inhibitor(s), and a retinoic acid derivative(s); and
    (ii) culturing the cells obtained in the step (i) in a medium containing one or more substances selected from the group consisting of BMP7, a GSK-3β inhibitor(s), and a retinoic acid derivative(s).

[9] The method of [8], wherein the step (ii) comprises the following steps of:
    (ii-1) culturing the cells obtained in the step (i) in a medium containing one or more substances selected from the group consisting of BMP7 and a GSK-3β inhibitor(s); and
    (ii-2) culturing the cells obtained in the step (ii-1) in a medium containing one or more substances selected from the group consisting of a TGFβ signaling activator(s) and a retinoic acid derivative(s).

[10] The method of [9], wherein the step (ii-1) is a step of performing the culturing in a medium containing BMP7 and a GSK-3β inhibitor(s), and the step (ii-2) is a step of performing the culturing in a medium containing a TGFβ signaling activator(s) and a retinoic acid derivative(s).

[11] The method of any one of [8] to [10], wherein the GSK3β inhibitor is CHIR99021.

[12] The method of any one of [8] to [11], wherein the retinoic acid derivative is AM580 or TTNPB.

[13] The method of any one of [7] to [12], wherein the pluripotent stem cells are induced pluripotent stem (iPS) cells.

[14] The method of [13], wherein the iPS cells are human iPS cells.

[15] A method for producing renal progenitor cells from pluripotent stem cells, comprising the following steps of:
    (i) culturing pluripotent stem cells in a medium containing one or more substances selected from the group consisting of Activin A, a GSK-3β inhibitor(s), and a retinoic acid derivative(s);
    (ii) culturing the cells obtained in the step (i) in a medium containing one or more substances selected from the group consisting of BMP7, a GSK-3β inhibitor(s), and a retinoic acid derivative(s); and
    (iii) culturing the cells obtained in the step (ii) in a medium containing a TGFβ signaling activator(s) and a BMP inhibitor(s).

[16] The method of [15], wherein the renal progenitor cells are SIX2-positive cells.

[17] The method of [15] or [16], wherein the cells obtained in the step (ii) are OSR1-positive cells.

[18] The method of any one of [15] to [17], wherein the TGFβ signaling activator is one or more substances selected from the group consisting of TGFβ1, TGFβ2, TGFβ3, IDE1, and IDE2.

[19] The method of any one of [15] to [18], wherein the BMP inhibitor is one or more substances selected from the group consisting of Dorsomorphin, Noggin, LDN193189, and DMH1.

[20] The method of any one of [15] to [17], wherein the TGFβ signaling activator is TGFβ1, and the BMP inhibitor is DMH1.

[21] The method of any one of [15] to [20], wherein the step (ii) includes the following steps of:
    (ii-1) culturing the cells obtained in the step (i) in a medium containing one or more substances selected from BMP7 and a GSK-3β inhibitor(s); and
    (ii-2) culturing the cells obtained in the step (ii-1) in a medium containing one or more substances selected from a TGFβ signaling activator(s) and a retinoic acid derivative(s).

[22] The method of [21], wherein the step (ii-1) is a step of performing the culturing in a medium containing BMP7 and a GSK-3β inhibitor(s), and the step (ii-2) is a step of performing the culturing in a medium containing a TGFβ signaling activator(s) and a retinoic acid derivative(s).

[23] The method of any one of [15] to [22], wherein the GSK3β inhibitor is CHIR99021.

[24] The method of any one of [15] to [23], wherein the retinoic acid derivative is AM580 or TTNPB.

[25] The method of any one of [15] to [24], wherein the pluripotent stem cells are induced pluripotent stem (iPS) cells.

[26] The method of [25], wherein the iPS cells are human iPS cells.

[27] A renal progenitor cell produced by the method of any one of [1] to [26].

[28] A pharmaceutical composition, which comprises renal progenitor cells produced by the method of any one of [1] to [26].

[29] A therapeutic drug for kidney diseases, which comprises renal progenitor cells produced by the method of any one of [1] to [26].

[30] A method for treating a kidney disease, comprising the step of administering renal progenitor cells produced by the method of any one of [1] to [26] to a patient in need of treatment.

[31] A renal progenitor cell produced by the method of any one of [1] to [26], for use in the treatment of kidney diseases.

[32] Use of renal progenitor cells produced by the method of any one of [1] to [26], in manufacture of a pharmaceutical composition for treatment of kidney diseases.

According to the present invention, it became possible for the first time to artificially induce renal progenitor cells from intermediate mesoderm cells. In addition, according to the present invention, it became possible for the first time to artificially induce renal progenitor cells from pluripotent stem cells (e.g., iPS cells). Further, it has been confirmed that the renal progenitor cells produced by the method of the present invention are effective for treatment in kidney disease animal models. The renal progenitor cells produced by the method of the present invention can be used in the treatment or regenerative medicine for kidney diseases including renal failure.

The present specification incorporates the contents described in the specifications and/or drawings of Japanese Patent Application Nos. 2013-123072 (Filing date: Jun. 11, 2013) and 2014-92108 (Filing date: Apr. 25, 2014) from which the present application claims priority.

BRIEF DESCRIPTION OF DRAWINGS

FIGS. 1A to 1D, shows the content of SIX2-positive cells induced by differentiation in Examples 2 to 4. FIG. 1A shows the results of culture in a medium containing DMSO as a control. FIG. 1B shows the results of differentiation induction via induction method 1 (Example 2). FIG. 1C shows the results of differentiation induction via induction method 2 (Example 3). FIG. 1D shows the results of differentiation induction via induction method 3 (Example 4). In each figure, tdTomato represents a reporter gene.

FIGS. 2A to 2H, shows the content of SIX2-positive cells induced by differentiation in Example 5. FIG. 2A shows the results of culture in a medium containing DMSO as a control. FIGS. 2B, 2C, and 2D show the results obtained using Noggin, LDN193189, and DMH1, respectively, in replace of Dorsomorphin, at stage 3 of induction method 1. FIGS. 2E and 2F show the results obtained using IDE1 and IDE2, respectively, in replace of TGFβ1, at stage 3 of induction method 1. FIG. 2G shows the results obtained using TGFβ2 and LDN193189 at stage 3 of induction method 1. FIG. 2H shows the results obtained using TGFβ3 and LDN193189 at stage 3 of induction method 1.

FIGS. 3A and 3B, shows an example of the method for producing OSR1$^+$SIX2$^+$ renal progenitor cells from human iPS cells. FIG. 3A shows a method for differentiation into OSR1$^+$SIX2$^+$ renal progenitor cells using three-dimensional culture of EBs (embryoid bodies). FIG. 3B shows the results of the time-course differentiation pattern analysis of OSR1$^+$SIX2$^+$ cells measured by flow cytometry, and specifically, the results of two-dimensional cell population distribution (n=5). FIG. 3C shows the results of the time-course analysis of mRNA expression for each of the indicated genes in differentiated cell populations. Each graph shows the expression levels of the gene relative to the β actin expression levels from Day 1 to Day 28 (n=3). FIG. 3D shows the results of the time-course differentiation pattern analysis of OSR1$^+$SIX2$^+$ cells measured by flow cytometry in Example 7, and more specifically, the results of the time course analysis of the cell populations (n=5). In FIG. 3D, d1 represents results for iPS cells on Day 1, and d3 represents results for EB (Day 3) produced in a medium (stage 1) containing CHIR99021 and Activin A. In FIG. 3D, d6 to d28 represent results for the DMSO group (referred to as "DMSO") and the TGFβ1+TTNPB treatment group (referred to as "Tx") from Day 6 to Day 28, respectively. Cells were cultured in a medium containing CHIR99021 and BMP7 at stage 2 for 3 days (Day 3 to Day 6), and then divided into a DMSO group and a Tx group on Day 6, followed by culture at stages 3 and 4. For the DMSO group, cells were cultured in a medium containing DMSO in replace of TGFβ1 and TTNPB at stage 3 (where the medium was exchanged with the same medium on Day 8), and then cultured in a medium containing DMSO in replace of TGFβ1 and DMH1 at stage 4 (where the medium was exchanged with the same medium every 3 days). FIG. 3E shows the expression of renal progenitor cell markers in OSR1$^+$SIX2$^+$ renal progenitor cells differentiated from 4A6C3-10 on Day 28 of culture.

FIGS. 5A and 5B, shows the results of the differentiation induction by induction method 4 using different human iPS cells and human ES cells (i.e., OSR1 expression levels (FIG. 5A) and SIX2 expression levels (FIG. 5B)). The results are the expression levels of OSR1 and SIX2 in each cell relative to the expression levels in 4A6C3-10.

FIGS. 6A to 6F, shows the evaluation test results of renal progenitor cells. FIG. 6A shows immunostaining images of OSR1$^+$SIX2$^+$ cells after cultured in REGM medium for 7 days. In this figure, NEPHRIN represents a glomerular podocyte marker, AQP1 and MEGALIN represent proximal tubule markers, and UROMUCOID represents a Henle's loop marker. These markers were stained pink, and nuclei were stained blue. The scale bar is 50 μm. FIG. 6B shows the microscopic image (the left panel) and the immunostaining images (the remaining 3 panels) after 7-day coculture of OSR1$^+$SIX2$^+$ cell mass and Wnt4-expressing NIH3T3. FIG. 6C shows the microscopic image (the left panel) and the immunostaining images (the remaining 3 panels) after 7-day coculture of OSR1$^+$SIX2$^+$ cell mass and E11.5 mouse embryonic spinal cord. FIG. 6D shows the immunostaining images after organ culture of OSR1$^+$SIX2$^+$ cell mass and E11.5 mouse embryonic metanephric cells. FIG. 6E shows the immunostaining image after transplantation of OSR1$^+$SIX2$^+$ cell mass into epididymal fat pads of NOD. CB17-Prkdc$^{scid}$/J. In this figure, WT1 and PODOCALYXIN (PODX) represent glomerular podocyte markers (red and pink, respectively), LTL represents a proximal tubule marker (red), LAMININ represents a polarized epithelium marker (pink), CDH1 represents a distal tubule marker (pink), CDH6 represents a renal vesicle marker (pink), and HuNu represents human nucleus (green), while mouse nucleus is stained blue, and the scale bar is 50 μm. FIG. 6F shows the microscopic images (the left panels) after 7-day organ culture of each cell mass of the iPS cells-derived fractions (OSR1$^-$SIX2$^-$, OSR1$^+$SIX2$^-$, OSR1$^-$SIX2$^+$, and OSR1$^+$SIX2$^+$) and an E11.5 mouse ureteric bud, and the immunostaining image (the right panel) after coculture of OSR1$^+$SIX2$^+$ cell mass and ureteric bud. In this figure, DBA represents a ureteric bud marker (red), and the scale bar is 50 μm. HuNu represents human nucleus (green), while mouse nucleus is stained blue.

FIGS. 7A to 7D, shows the results of experiments for transplantation into kidney disease mouse models. FIGS. 7A and 7B show the immunostaining images of kidney sections of acute kidney injury (AKI) mouse models (FIG. 7A) and chronic renal failure mouse models (FIG. 7B), which models are at two weeks after transplantation of OSR1$^+$SIX2$^+$ cell mass into the kidney parenchyma. LTL and AQP1 represent proximal tubule markers, which are stained green and red, respectively. HuNu represents human nucleus (pink). The scale bar is 50 μm. FIG. 7C shows the results of the time-course analyses of BUN levels and serum Cr levels for AKI mouse models subjected to renal subcapsule transplantation of hiPSC-RP (n=10, iPSC-RPs, triangle), undifferentiated human iPS cells (n=10, iPSCs, square), or physiological saline (n=10, Saline, circle) [*P<0.05, P<0.01, *P<0.001 vs Saline]. FIG. 7D shows the histological findings for kidney tissues derived from mouse which was subjected to transplantation of hiPSC-RP (iPSC-RPs) or physiological saline (Saline). Kidney tissues were stained with Periodic acid-Schiff (PAS, upper panels) or Masson's trichrome (MT, lower panels) on day 3 after ischemia-reperfusion (I/R). FIG. 7E shows the results of determination of the area of dilated tubules with casts or fibrosis in the host kidneys on day 3 after I/R [**P<0.01 vs Saline, n=3 per group].

MODE FOR CARRYING OUT INVENTION

Figure 1:
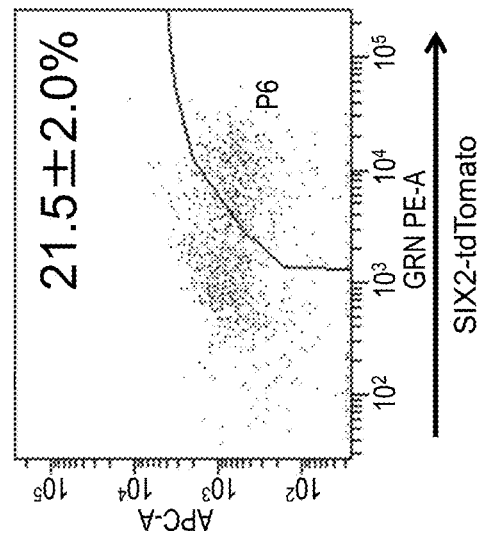
FIG. 1, including
Figure 1:
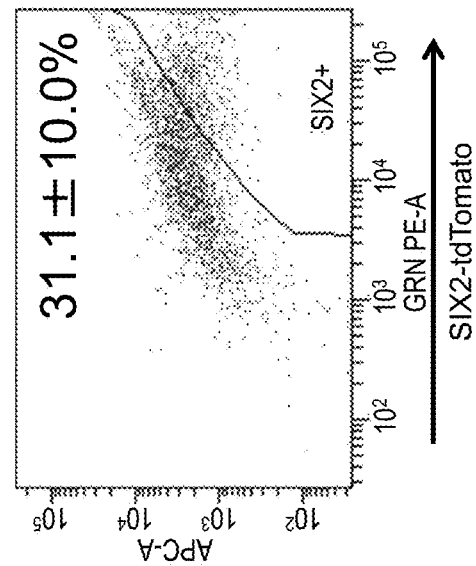
Figure 1:
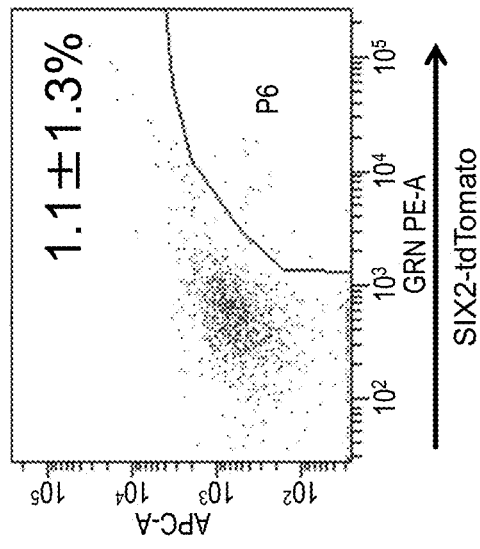
Figure 1:
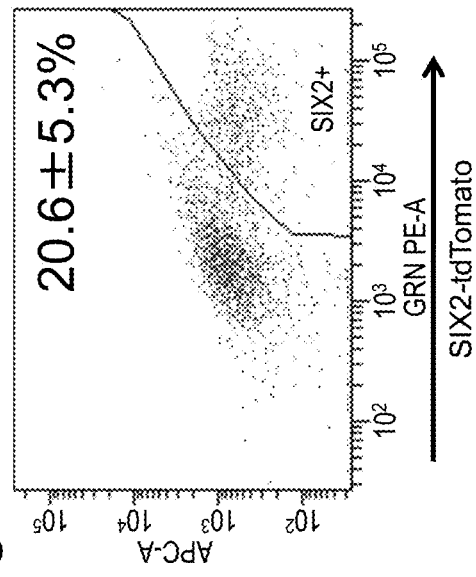

The present invention will be described in detail below.

The present invention provides a method for producing renal progenitor cells, which comprises a step of culturing intermediate mesoderm cells in a medium containing a TGFβ signaling activator(s) and a BMP inhibitor(s).

The term "intermediate mesoderm cells" as used herein refers to any cells from which renal progenitor cells are induced, when cultured in a medium containing a TGFβ signaling activator(s) and a BMP inhibitor(s) according to the invention. Examples of known methods for obtaining intermediate mesoderm cells include methods for inducing differentiation of mouse and human pluripotent stem cells into intermediate mesoderm cells (Non-Patent Documents 1 and 2, and Patent Document 3). OSR1 is known as a marker that characterizes intermediate mesoderm cells, and examples of the intermediate mesoderm cells used in the method of the invention include intermediate mesoderm cells which are OSR1-positive. For example, it is possible to culture pluripotent stem cells (e.g., OSR1-GFP reporter human iPS cells described in the Examples below) having a reporter gene (e.g., GFP) introduced under the control of an OSR1 promotor and then isolate intermediate mesoderm cells which are OSR1-positive using, as an indicator, expression of the reporter gene by methods known in the art (e.g., methods using cell sorter). It is also possible to confirm OSR1 expression in intermediate mesoderm cells using methods of analyzing gene expression, such as quantitative RT-PCR (Nat Commun 4, 1367, (2013)). In the present invention, the intermediate mesoderm cells which are OSR1-positive include cells expressing an OSR1 protein and cells expressing a protein encoded by a gene under the control of OSR1 promotor. In the present invention, examples of OSR1 include genes having the nucleotide sequences under NCBI Accession Nos. NM_145260.2 (human) and NM_011859.3 (mouse), proteins encoded by the genes, and naturally occurring variants having functions of such genes. Preferably, the intermediate mesoderm cells used in the method of the invention are SIX2-negative and OSR1-positive cells.

In the present invention, the renal progenitor cells are cells that can be handled as cells equivalent to nephron progenitor cells and can differentiate in vitro into organ structures, such as glomerulus-like structure and tubule-like structure, of kidney. Capacity to differentiate into an organ structure can be evaluated by, for example, the method disclosed in Osafune K, et al. (2006), Development 133: 151-61. A known characteristic factor for maintaining the state of nephron progenitor cells is SIX2 (Non-Patent Document 4). Examples of the renal progenitor cells induced by the method of the invention include SIX2-positive renal progenitor cells. For example, it is possible to culture pluripotent stem cells (e.g., OSR1-GFP & SIX2-tdTomato reporter human iPS cells as described in the Examples below) having a reporter gene (e.g., tdTomato) introduced under the control of an SIX2 promotor and then isolate SIX2-positive renal progenitor cells using, as an indicator, expression of the reporter gene by methods known in the art (e.g., methods using cell sorter). It is also possible to confirm SIX2 expression in renal progenitor cells by methods for analyzing gene expression such as quantitative RT-PCR (Nat Commun 4, 1367, (2013)). In the present invention, the SIX2-positive renal progenitor cells include cells expressing SIX2 protein and cells expressing a protein encoded by a gene under the control of SIX2 promotor. In the present invention, examples of SIX2 include genes having the nucleotide sequences under NCBI Accession Nos. NM_016932.4 (human) and NM_011380.2 (mouse), proteins encoded by the genes, and naturally occurring variants having functions of such genes. Preferably, the renal progenitor cells induced by the method of the invention are OSR1-positive and SIX2-positive cells.

In the present invention, the intermediate mesoderm cells or the renal progenitor cells may be provided in the form of a cell population comprising other kinds of cells or a purified cell population, and in this case, preferably, the intermediate mesoderm cells or the renal progenitor cells are contained in the amount of 5% or more, 6% or more, 7% or more, 8% or more, 9% or more, and 10%, 20%, 28%, or 30% or more in the cell population.

In the method of the invention, intermediate mesoderm may be cultured by suspension culture or by adhesion culture using coated culture dishes in the state of single cells which are substantially dissociated (or separated) using any method or in the state of cell mass in which cells are attached each other. Here, the methods for dissociating intermediate mesoderm cells involve, for example, mechanical dissociation methods, and dissociation methods using a dissociation solution having protease activity and collagenase activity (e.g., a solution containing trypsin and collagenase, such as Accutase™ or Accumax™ (Innovative Cell Technologies, Inc.)) or a dissociation solution having collagenase activity alone.

The suspension culture used in the method of the present invention means culturing cells in a non-adherent manner in a culture dish. Examples of the culture dish that can be used include, but are not limited to, a culture dish without artificial treatment (e.g., coating with an extracellular matrix or the like) for improving adhesion to cells, and a culture dish artificially treated for preventing adhesion (e.g., coating with poly(hydroxyethyl methacrylate) (poly-HEMA)).

The adhesion culture used in the method of the present invention means culturing cells on a coated culture dish. Examples of coating agents include Matrigel (BD Biosciences), Synthemax (Corning), collagen, gelatin, laminin, heparan sulfate proteoglycan, entactin, and combinations thereof. Preferably, the coating agents are Matrigel, Synthemax, or gelatin.

A medium used in the step of culturing intermediate mesoderm cells in the invention can be prepared by adding a TGFβ signaling activator(s) and a BMP inhibitor(s) to a basal medium for culture of animal cells. Examples of the basal medium include IMDM, Medium 199, Eagle's Minimum Essential Medium (EMEM), αMEM, Dulbecco's Modified Eagle's Medium (DMEM), Ham's F12 (F12), RPMI 1640, Fischer's medium, and mixtures thereof. The medium may contain serum (e.g., fetal bovine serum (FBS)) or may be serum-free. Where needed, the medium may contain one or more serum replacements, such as albumin, transferrin, KnockOut Serum Replacement (KSR) (a serum replacement for ES cell culture) (Invitrogen), N2 supplement (Invitrogen), B27 supplement (Invitrogen), fatty acids, insulin, collagen precursors, trace elements, 2-mercaptoethanol, and 3'-thioglycerol, and it may further contain one or more other substances, such as lipids, amino acids, L-glutamine, GlutaMAX (Invitrogen), non-essential amino acids (NEAAs), vitamins, growth factor, antibiotic, antioxidant, pyruvic acid, buffering agents, inorganic salts, and equivalents thereof. In one embodiment, the basal medium is a mixture containing DMEM and F12 at 1:1 (DMEM/F12) supplemented with GlutaMAX, KSR, non-essential amino acids, 2-mercaptoethanol, and antibiotic.

The TGFβ signaling activator used in the present invention is not particularly limited as long as it activates the TGFβ signaling pathway. Examples of the TGFβ signaling activator include proteins, such as TGFβ1, TGFβ2, and TGFβ3 (available from Peprotech, R&D, etc.), and compounds, such as IDE1 ((Z)-2-((2-(6-carboxyhexanoyl)hydrazono)methyl)benzoic acid) and IDE2 (7-(2-cyclopentylidenehydrazinyl)-7-oxoheptanoic acid) (Borowiak M, et al, Cell Stem Cell. 2009, 4: 348-58). IDE1 and IDE2 are available from Stemgent, Tocris, etc. Preferable TGFβ signaling activator is TGFβ1.

In the present invention, the concentration of a TGFβ signaling activator may be appropriately determined by a person skilled in the art depending on TGFβ signaling activators to be used. Where a protein, such as TGFβ1, TGFβ2, or TGFβ3, is used as the TGFβ signaling activator, its concentration is, for example, 0.1 ng/ml to 100 ng/ml, preferably 1 ng/ml to 10 ng/ml, more preferably 5 ng/ml to 10 ng/ml. In addition, where IDE1 or IDE2 is used as the TGFβ signaling activator, its concentration is 1 µM to 100 µM, preferably 25 µM to 75 µM, more preferably 40 µM to 60 µM.

The BMP inhibitor used in the present invention is not particularly limited as long as it inhibits the BMP (Bone Morphogenetic Protein) signaling pathway. Examples of the BMP inhibitor include: inhibitor proteins such as Chordin, Noggin, and Follistatin; Dorsomorphin (6-[4-(2-piperidin-1-yl-ethoxy)phenyl]-3-pyridin-4-yl-pyrazolo[1,5-a]pyrimidine) and derivatives thereof (P. B. Yu et al. (2007), Circulation, 116: II_60; P. B. Yu et al. (2008), Nat. Chem. Biol., 4: 33-41; J. Hao et al. (2008), PLoS ONE, 3 (8): e2904); DMH1 (4-[6-(4-Isopropoxyphenyl)pyrazolo[1,5-a]pyrimidin-3-yl]quinolone, 4-[6-[4-(1-Methylethoxy)phenyl]pyrazolo[1,5-a]pyrimidin-3-yl]-quinoline); and LDN193189 (4-(6-(4-(piperazin-1-yl)phenyl)pyrazolo[1,5-a]pyrimidin-3-yl)quinoline). Dorsomorphin and LDN193189 are commercially available from Sigma-Aldrich, Stemgent, Merck, Axon Medchem, Peprotech, etc. Preferably, the BMP inhibitor is DMH1, Noggin, LDN193189, or Dorsomorphin, more preferably DMH1.

In the present invention, the concentration of a BMP inhibitor used may be appropriately determined by a person skilled in the art depending on BMP inhibitors to be used. Where an inhibitor protein, such as Chordin, Noggin, or Follistatin, is used as the BMP inhibitor, its concentration is, for example, 0.1 ng/ml to 1000 ng/ml, preferably 1 ng/ml to 500 ng/ml, more preferably 10 ng/ml to 100 ng/ml. In addition, where Dorsomorphin, DMH1, or LDN193189 is used as the BMP inhibitor, its concentration is 0.01 µM to 100 µM, preferably 0.1 µM to 10 µM, more preferably 0.5 µM to 1 µM.

In the step of culturing intermediate mesoderm cells in the invention, any one of or any combination of FGF9, FGF20, BMP7, a retinoic acid derivative, and a GSK-3β inhibitor may be added to a basal medium.

In the present invention, there is no upper limit of culture days in the step of culturing intermediate mesoderm cells, because long-term culture does not particularly affect a production efficiency of renal progenitor cells. The culture days are, for example, 2 days or more, 4 days or more, 6 days or more, 8 days or more, 10 days or more, 11 days or more, 12 days or more, 13 days or more, 14 days or more, 15 days or more, 16 days or more, 17 days or more, 18 days or more, 19 days or more, or 20 days or more.

In the step of culturing intermediate mesoderm cells, the culture temperature is, but not limited to, about 30° C. to about 40° C. and preferably about 37° C. Culture is carried out in an atmosphere of $CO_2$-containing air. The $CO_2$ concentration is preferably about 2% to about 5%.

In one embodiment of the present invention, the intermediate mesoderm cells are intermediate mesoderm cells induced from pluripotent stem cells. In this case, the induced intermediate mesoderm cells may be isolated, followed by inducing renal progenitor cells from the isolated intermediate mesoderm cells in the culture step of the present invention. Alternatively, intermediate mesoderm cells may be induced from pluripotent stem cells, followed by directly subjecting the intermediate mesoderm cells, without isolating them, to the culture step of the present invention so as to induce renal progenitor cells.

When the intermediate mesoderm cells are isolated, pluripotent stem cells which have a reporter gene that is expressed under the control of an endogenous OSR1 promotor may be used. An example of a method for introducing a reporter gene under the control of an OSR1 promotor in pluripotent stem cells is homologous recombination using a BAC vector or the like, which is disclosed in, for example, WO2012/011610. In addition, in order to isolate the induced renal progenitor cells, pluripotent stem cells which have a reporter gene that is expressed under the control of an SIX2 promotor may be used. Such pluripotent stem cells may be prepared by the methods described above. Examples of the reporter gene to be used include genes encoding known reporter proteins, such as β-galactosidase, β-glucosidase, luciferase, green fluorescent protein (GFP), tdTomato, and cell surface proteins. The intermediate mesoderm cells or the renal progenitor cells, which are induced from the above pluripotent stem cells, can be isolated by methods known in the art, such as a method using a cell sorter which uses expression of the reporter protein as an indicator, a method for sorting cells using an antibody against the cell surface protein via magnetic properties of magnetic beads (e.g., MACS), and a method using a carrier on which the antibody or the like is immobilized (e.g., a cell enrichment column).

The term "pluripotent stem cells" as used herein refers to stem cells having pluripotency capable of differentiating into various types of cells present in living bodies, as well as a proliferation capacity, including any pluripotent stem cells from which intermediate mesoderm cells usable in the invention are induced. Examples of pluripotent stem cells include, but are not particularly limited to, embryonic stem (ES) cells, nuclear transfer embryonic stem (ntES) cells derived from cloned embryos, germline stem cells ("GS cells"), embryonic germ cells ("EG cells"), induced pluripotent stem (iPS) cells, and cultured fibroblast-derived or bone-marrow-stem-cell-derived pluripotent cells (Muse cells). Preferably, the pluripotent stem cells are iPS cells, from the view point that the iPS cells can be obtained without destroying embryos, ova (or eggs), or the like, upon production. More preferably, the pluripotent stem cells are human iPS cells.

Methods for producing iPS cells are known in the art, and thus iPS cells can be produced by introducing reprogramming factors into any of somatic cells. Here, examples of the reprogramming factors include the following genes or gene products: Oct3/4, Sox2, Sox1, Sox3, Sox15, Sox17, Klf4, Klf2, c-Myc, N-Myc, L-Myc, Nanog, Lin28, Fbx15, ERas, ECAT15-2, Tcl1, beta-catenin, Lin28b, Sall1, Sall4, Esrrb, Nr5a2, Tbx3, and Glis1. These reprogramming factors may be used alone or in combination. Examples of a combination of reprogramming factors are described in the following documents: WO2007/069666, WO2008/118820, WO2009/007852, WO2009/032194, WO2009/058413; WO2009/057831; WO2009/075119; WO2009/079007; WO2009/091659; WO2009/101084; WO2009/101407; WO2009/102983; WO2009/114949; WO2009/117439; WO2009/126250; WO2009/126251; WO2009/126655; WO2009/157593; WO2010/009015; WO2010/033906; WO2010/033920; WO2010/042800; WO2010/050626; WO2010/056831; WO2010/068955; WO2010/098419; WO2010/102267; WO 2010/111409; WO2010/111422; WO2010/115050; WO2010/124290; WO2010/147395; WO2010/147612; Huangfu, D, et al. (2008), Nat. Biotechnol., 26: 795-797, Shi, Y, et al. (2008), Cell Stem Cell, 2: 525-528; Eminli, S, et al. (2008), Stem Cells. 26: 2467-2474;

Huangfu, D, et al. (2008), Nat. Biotechnol. 26: 1269-1275; Shi, Y, et al. (2008), Cell Stem Cell, 3, 568-574; Zhao, Y, et al. (2008), Cell Stem Cell, 3: 475-479; Marson, A, (2008), Cell Stem Cell, 3, 132-135; Feng, B, et al. (2009), Nat. Cell Biol. 11: 197-203; Judson, R L, et al., (2009), Nat. Biotechnol., 27: 459-461; Lyssiotis, C A, et al. (2009), Proc Natl Acad Sci USA 106: 8912-8917; Kim, J B, et al. (2009), Nature 461: 649-643; Ichida, J K, et al. (2009), Cell Stem Cell 5: 491-503; Heng, J C, et al. (2010), Cell Stem Cell 6: 167-74; Han, J, et al. (2010), Nature 463: 1096-100; Mali, P, et al. (2010), Stem Cells 28: 713-720; and Maekawa, M, et al. (2011), Nature 474: 225-9.

Examples of somatic cells include, but are not limited to, any of fetal somatic cells, neonatal somatic cells, and mature healthy or affected somatic cells, which may be primary cultured cells, subcultured cells, or established cells. Specifically, examples of somatic cells include: (1) tissue stem cells (or somatic stem cells) such as neural stem cells, hematopoietic stem cells, mesenchymal stem cells, and dental pulp stem cells; (2) tissue progenitor cells; and (3) differentiated cells such as hematocytes (e.g., peripheral blood cells and umbilical cord blood cells), lymphocytes, epithelial cells, endothelial cells, muscle cells, fibroblasts (e.g., skin cells), hair cells, hepatocytes, gastric mucosal cells, enterocytes, spleen cells, pancreatic cells (e.g., pancreatic exocrine cells), brain cells, lung cells, kidney cells, and fat cells.

In addition, when iPS cells are used as material for transplantation cells, it is preferable to use somatic cells having an HLA genotype that is identical or substantially identical to that of a recipient in order to avoid rejection. The expression "substantially identical" used herein means correspondence of HLA genotypes to an extent that immunoreaction of transplanted cells can be suppressed using an immunosuppressant. For example, somatic cells having the HLA genotype showing that three gene loci, i.e. HLA-A, HLA-B, and HLA-DR, or four gene loci including the three aforementioned gene loci and HLA-C are identical to those of a recipient can be used.

In the present invention, a method comprising the following steps can be used for inducing differentiation of pluripotent stem cells into intermediate mesoderm cells:

(i) culturing pluripotent stem cells in a medium containing one or more substances selected from the group consisting of Activin A, a GSK-3β inhibitor(s), and a retinoic acid derivative(s); and (ii) culturing the cells obtained in the step (i) in a medium containing one or more substances selected from the group consisting of BMP7, a GSK-3β inhibitor(s), and a retinoic acid derivative(s).

Each step is described in more detail below.

(i) Step of Culturing Pluripotent Stem Cells in a Medium Containing One or More Substances Selected from the Group Consisting of Activin A, a GSK-3β Inhibitor(s), and a Retinoic Acid Derivative(s):

In this step, pluripotent stem cells may be dissociated by a method known in the art and then cultured by suspension culture or adhesion culture. Examples of a method for dissociating pluripotent stem cells include mechanical dissociation and dissociation with the use of a dissociation solution having protease activity and collagenase activity (e.g., Accutase™ or Accumax™ (Innovative Cell Technologies, Inc.)) or a dissociation solution having collagenase activity alone. Preferably, the method for the dissociation is a method comprising dissociating cells using a dissociation solution having protease activity and collagenase activity and dispersing the cells into single cells in a mechanical manner making fine is used. Preferably, the human pluripotent stem cells used in this step are colonies cultured so as to become 70% to 80% confluent on a dish to be used.

A medium used in step (i) can be prepared by adding one or more substances selected from the group consisting of Activin A, a GSK-3β inhibitor(s), and a retinoic acid derivative(s) to a basal medium for animal cell culture. In one embodiment, substances used in this step are: a combination of Activin A and a GSK-3β inhibitor(s); or a combination of a GSK-3β inhibitor(s) and a retinoic acid derivative(s). Examples of a basal medium include IMDM, Medium 199, Eagle's Minimum Essential Medium (EMEM), αMEM, Dulbecco's Modified Eagle's Medium (DMEM), Ham's F12 (F12), RPMI 1640, Fischer's medium, and mixtures thereof. The medium may contain serum (e.g., FBS) or may be serum-free. If necessary, the medium may contain one or more serum replacements, such as albumin, transferrin, KnockOut Serum Replacement (KSR) (which is a serum replacement for ES cells culture) (Invitrogen), N2 supplement (Invitrogen), B27 supplement (Invitrogen), fatty acids, insulin, collagen precursors, trace elements, 2-mercaptoethanol, and 3'-thioglycerol, and may further contain one or more other substances, such as lipids, amino acids, L-glutamine, GlutaMAX (Invitrogen), non-essential amino acids (NEAAs), vitamins, growth factor, low-molecular-weight compounds, antibiotic, antioxidant, pyruvic acid, buffering agent, or inorganic salts. In one embodiment of this step, the basal medium is DMEM/F12 containing GlutaMAX, serum, and antibiotic.

In the step (i), examples of Activin A include human- or another animal-derived Activin A and functional variants thereof. For example, Activin A, which is commercially available from R&D Systems, etc., can be used. The concentration of Activin A used in this step is 1 ng/ml to 1000 ng/ml, preferably 10 ng/ml to 500 ng/ml, more preferably 50 ng/ml to 200 ng/ml.

In the step (i), the GSK-3β inhibitor is not particularly limited as long as it can inhibit a function of GSK-3β such as kinase activity. Examples of the GSK-3β inhibitor include BIO (another name, GSK-3β inhibitor IX; 6-bromoindirubin-3'-oxime) which is an indirubin derivative, SB216763 (3-(2,4-dichlorophenyl)-4-(1-methyl-1H-indole-3-yl)-1H-pyrrole-2,5-dione) which is a maleimide derivative, GSK-3β inhibitor VII (α,4-dibromoacetophenone) which is a phenyl-α-bromomethyl ketone compound, L803-mts (another name, GSK-3β peptide inhibitor; Myr-N-GKEAP-PAPPQSpP-NH$_2$: SEQ ID NO. 1) which is a cell-penetrating phosphorylated peptide, and CHIR99021 (Nature (2008) 453: 519-523) having high selectivity. These compounds are available from, for example, Stemgent, Calbiochem, and Biomol, or alternatively, they may be self-prepared. The preferable GSK-3β inhibitor used in this step is CHIR99021. The concentration of a GSK-3β inhibitor used in this step can be appropriately determined by a person skilled in the art depending on GSK-3β inhibitors to be used. For example, when CHIR99021 is used as the GSK-3β inhibitor, its concentration is 0.01 μM to 100 μM, preferably 0.1 μM to 10 μM, more preferably 1 μM to 3 μM.

In the step (i), the retinoic acid derivatives may be artificially modified retinoic acids that maintain the function of naturally occurring retinoic acid, such as retinoid compounds or vitamin D3 compounds. Examples of retinoid compounds include retinoic acid, 3-dehydro retinoic acid, 4-[[(5,6,7,8-tetrahydro-5,5,8,8-tetramethyl-2-naphthalenyl) carbonyl]amino]-Benzoic acid (AM580) (Tamura, K. et al., Cell Differ. Dev. 32: 17-26 (1990)), 4-[(1E)-2-(5,6,7,8-tetrahydro-5,5,8,8-tetramethyl-2-naphthalenyl)-1-propen-1- yl]-Benzoic acid (TTNPB) (Strickland S, et al., Cancer Res. 43: 5268-5272 (1983)), compounds described in Tanenaga, K. et al., Cancer Res. 40: 914-919 (1980), retinol palmitate, retinol, retinal, 3-dehydroretinol, and 3-dehydroretinal. Examples of retinoic acid compounds include a retinoid compound having a carboxyl group, such as retinoic acid, 3-dehydro retinoic acid, AM580, or TTNPB. Examples of vitamin D3 compounds include compounds described in Abe, E., et al., Proc. Natl. Acad. Sci. (USA) 78: 4990-4994 (1981) and compounds described in Schwartz, E. L. et al., Proc. Am. Assoc. Cancer Res. 24: 18 (1983). In one embodiment of this step, a retinoic acid derivative is a retinoid compound or a vitamin D3 compound. In another embodiment of this step, the retinoic acid derivative is a retinoid compound. Also in another embodiment, the retinoic acid derivative is a retinoic acid compound. Examples of a preferable retinoic acid derivative used in this step include AM580 or TTNPB. The concentration of the retinoic acid derivative used in this step can be appropriately determined by a person skilled in the art depending on retinoic acid derivatives to be used. For example, when AM580 or TTNPB is used as the retinoic acid derivative, its concentration is 0.01 µM to 100 µM, preferably 0.1 µM to 10 µM, more preferably 0.5 µM to 2 µM.

The medium used in the step (i) may further contain a ROCK inhibitor. In particular, when this step includes a step of dispersing pluripotent stem cells into single cells, it is preferable to contain a ROCK inhibitor in the medium.

The ROCK inhibitor is not particularly limited as long as it can inhibit the function of Rho-kinase (ROCK), and its examples include: Y-27632 (see, e.g., Ishizaki et al., Mol. Pharmacol. 57, 976-983 (2000); Narumiya et al., Methods Enzymol. 325,273-284 (2000)), Fasudil/HA1077 (see, e.g., Uenata et al., Nature 389: 990-994 (1997)), H-1152 (see, e.g., Sasaki et al., Pharmacol. Ther. 93: 225-232 (2002)), Wf-536 (see, e.g., Nakajima et al., Cancer Chemother Pharmacol. 52(4): 319-324 (2003)), and derivatives thereof; and antisense nucleic acids, nucleic acids inducing RNA interference (e.g., siRNA), and dominant negative mutants of ROCK, and expression vectors for them. In addition, other known low-molecular-weight compounds can also be used as ROCK inhibitors (see, for example, US Patent Publication No. 2005/0209261, US Patent Publication No. 2005/0192304, US Patent Publication No. 2004/0014755, US Patent Publication No. 2004/0002508, US Patent Publication No. 2004/0002507, US Patent Publication No. 2003/0125344, US Patent Publication No. 2003/0087919, WO2003/062227, WO2003/059913, WO2003/062225, WO2002/076976, and WO2004/039796). In the present invention, one or two or more types of ROCK inhibitors can be used. A preferable example of the ROCK inhibitor used in this step is Y-27632. The concentration of a ROCK inhibitor used in this step can be appropriately determined by a person skilled in the art depending on ROCK inhibitors to be used. For example, when Y-27632 is used as the ROCK inhibitor, its concentration is 0.1 µM to 100 µM, preferably 1 µM to 50 µM, more preferably 5 µM to 20 µM.

The culture temperature in the step (i) may be, but is not limited to, about 30° C. to about 40° C. and preferably about 37° C., and culture is carried out in an atmosphere of $CO_2$-containing air. The $CO_2$ concentration is about 2% to about 5% and preferably about 5%. The culture period in this step is, for example, 2 days or less and preferably 2 days.

(ii) Step of Culturing the Cells Obtained in the Step (i) in a Medium Containing One or More Substances Selected from the Group Consisting of BMP7, a GSK-3β Inhibitor(s), and a Retinoic Acid Derivative(s):

In this step, the cell population per se obtained after suspension culture in the step (i) above may be subjected to adhesion culture on a coated culture dish containing any of the media, or alternatively, the cells obtained by adhesion culture in the step (i) may be continued to culture them while the medium is exchanged.

A medium used in the step (ii) can be prepared by adding one or more substances selected from the group consisting of BMP7, a GSK-3β inhibitor(s), and a retinoic acid derivative(s) to a basal medium for animal cell culture. In one embodiment, substances used in this step are a combination of BMP7 and a GSK-3β inhibitor(s), or a retinoic acid derivative(s). Examples of the basal medium include IMDM, Medium 199, Eagle's Minimum Essential Medium (EMEM), αMEM, Dulbecco's Modified Eagle's Medium (DMEM), Ham's F12 (F12), RPMI 1640, Fischer's medium, and mixtures thereof. The medium may contain serum (e.g., FBS) or may be serum-free. If necessary, the medium may contain one or more serum replacements, such as albumin, transferrin, KnockOut Serum Replacement (KSR) (which is a serum replacement for ES cell culture) (Invitrogen), N2 supplement (Invitrogen), B27 supplement (Invitrogen), fatty acids, insulin, collagen precursors, trace elements, 2-mercaptoethanol, or 3'-thioglycerol, or may further contain one or more other substances, such as lipids, amino acids, L-glutamine, GlutaMAX (Invitrogen), non-essential amino acids (NEAAs), vitamins, growth factor, antibiotic, antioxidant, pyruvic acid, buffering agent, inorganic salts, or equivalents thereof. In one embodiment of this step, the basal medium is a mixture containing DMEM and F12 at 1:1 (DMEM/F12) supplemented with GlutaMAX, KSR, non-essential amino acids, 2-mercaptoethanol, and antibiotic.

In the step (ii), for example, the cells obtained in the step (i) may be cultured in a medium containing one or more substances selected from BMP7 and a GSK-3β inhibitor(s), then in a medium containing a retinoic acid derivative(s). Preferably, in the step (ii), the cells obtained in the step (i) are cultured in a medium containing one or more substances selected from BMP7 and a GSK-3β inhibitor(s), then in a medium containing a retinoic acid derivative(s) and a TGFβ signaling activator(s).

Thus, the step (ii) may be separated into the following steps of:

(ii-1) culturing the cells in a medium containing one or more substances selected from BMP7 and a GSK-3β inhibitor(s); and (ii-2) culturing the cells in a medium containing one or more substances selected from a TGFβ signaling activator(s) and a retinoic acid derivative(s).

More preferably, in the step (ii), the step (ii-1) is a step of culturing the cells in a medium containing BMP7 and a GSK-3β inhibitor(s), and the step (ii-2) is a step of culturing the cells in a medium containing a TGFβ signaling activator (s) and a retinoic acid derivative(s).

In the step (ii), examples of BMP7 include human BMP7 (NCBI Accession No.: NM_001719.2), another animal-derived BMP7, and functional variants thereof. For example, BMP7 commercially available from Invitrogen, R&D, etc. can be used. The concentration of BMP7 used in this step is 1 ng/ml to 1000 ng/ml, preferably 10 ng/ml to 500 ng/ml, more preferably 50 ng/ml to 200 ng/ml.

In the step (ii), the GSK-3β inhibitors as exemplified in the step (i) above can be used. Preferable GSK-3β inhibitor is CHIR99021. The concentration of a GSK-3β inhibitor used in this step can be appropriately determined by a person skilled in the art depending on GSK-3β inhibitors to be used.

For example, when CHIR99021 is used as the GSK-3β inhibitor, its concentration is 0.01 μM to 100 μM, preferably 0.1 μM to 10 μM, more preferably 1 μM to 3 μM.

In step (ii), the TGFβ signaling activator is not particularly limited as long as it activates the TGFβ signaling pathway. Examples of the TGFβ signaling activator that can be used include: TGFβ1, TGFβ2, and TGFβ3; or IDE1 and IDE2. Preferable TGFβ signaling activator is TGFβ1. In the step (ii), the concentration of a TGFβ signaling activator to be used can be appropriately determined by a person skilled in the art depending on TGFβ signaling activators to be used. For example, when a protein such as TGFβ1, TGFβ2, or TGFβ3 is used as the TGFβ signaling activator, its concentration is 0.1 ng/ml to 100 ng/ml, preferably 1 ng/ml to 10 ng/ml, more preferably 5 ng/ml to 10 ng/ml. In addition, when IDE1 or IDE2 is used, its concentration is 1 μM to 100 μM, preferably 25 μM to 75 μM, more preferably 40 μM to 60 μM.

In the step (ii), the retinoic acid derivatives as exemplified in the step (i) can be used. Preferable retinoic acid derivative is AM580 or TTNPB. The concentration of a retinoic acid derivative used in this step can be appropriately determined by a person skilled in the art depending on retinoic acid derivatives to be used. For example, when AM580 or TTNPB is used as the retinoic acid derivative, its concentration is 0.01 μM to 100 μM, preferably 0.1 μM to 10 μM, more preferably 0.5 μM to 2 μM.

In the steps (ii), (ii-1) and (ii-2), the culture temperature may be, but is not limited to, about 30° C. to about 40° C., preferably about 37° C., and culture is carried out in an atmosphere of $CO_2$-containing air. The $CO_2$ concentration is about 2% to about 5%, preferably about 5%. There is no upper limit for the culture period because long-term culture does not particularly affect production efficiency of renal progenitor cells. For example, the culture period in the step (ii) is 3 days or more, preferably from 3 days or more to 12 days or less, more preferably from 3 days or more to 9 days or less. When the step (ii) comprises steps (ii-1) and (ii-2), the culture period in step (ii) is as described above, while the culture period in step (ii-1) is, for example, 1 day or more, preferably from 2 days or more to 11 days or less, more preferably from 2 days or more to 6 days or less, and the culture period in step (ii-2) is, for example, 1 day or more, preferably from 2 days or more to 11 days or less, more preferably from 3 days or more to 6 days or less. In this case, a medium is desirably exchanged every 3 days.

According the present invention, provided are: renal progenitor cells obtained by the methods described above; a pharmaceutical composition comprising the renal progenitor cells; a therapeutic drug for kidney diseases comprising the renal progenitor cells; a method for treating a kidney disease comprising a step of administering an therapeutically effective amount of the renal progenitor cells; the renal progenitor cells for use in treatment of kidney diseases; and use of the renal progenitor cells in manufacture of pharmaceutical compositions for treatment of kidney diseases. Examples of a method for administering the therapeutic drug to patients in need of treatment include: a method comprising preparing a sheet or sheets of the obtained renal progenitor cells and applying the sheet or sheets to kidneys of patients; a method comprising transplanting to patients directly a cell suspension, which is prepared by suspending the obtained renal progenitor cells in physiological saline or the like, or cell mass, which is prepared by three-dimensional culture of the obtained renal progenitor cells (e.g., Dev Cell. Sep. 11, 2012; 23 (3): 637-651), into kidneys of patients; and a method of transplanting the renal progenitor cell mass prepared by three-dimensional culture on a scaffold composed of Matrigel or the like. The transplantation site is not particularly limited as long as it is inside the kidney, however, and preferably, it is a renal subcapsule. Examples of kidney diseases include acute kidney injury, chronic renal failure, and chronic kidney diseases that do not reach the chronic renal failure stage.

According to the present invention, the number of renal progenitor cells contained in a therapeutic drug for kidney diseases is not particularly limited as long as graft engraftment is achieved after administration. It can be appropriately increased or decreased in accordance with the patient's lesion or body size.

EXAMPLES

The present invention is described in more detail with reference to the Examples below. However, the scope of the present invention is not limited thereto.

Example 1

Establishment of the OSR1-GFP & SIX2-GFP Knock-In Human iPS Cell Line

Human iPS cells (201B7) were given from Professor Shinya Yamanaka, Kyoto University (Kyoto, Japan), and they were cultured by a conventional method (Takahashi K, et al. Cell. 131: 861-72). Subsequently, an OSR1-GFP reporter human iPS cell line, which is capable of expression of GFP operably linked with expression of endogenous OSR1, was prepared by the method disclosed in Mae S, et al, Nat Commun. 4: 1367, 2013. Then, as disclosed by Mae et al (ibid), IRES-tdTomato was introduced downstream of the stop codon of SIX2 of the OSR1-GFP reporter human iPS cell line by homologous recombination using a BAC clone (RP11-819H19, Children's Hospital Oakland Research Institute) into which the IRES-tdTomato had been inserted, thereby producing an OSR1-GFP & SIX2-tdTomato reporter human iPS cell line that is capable of expression of tdTomato operably linked with expression of endogenous SIX2.

Example 2

SIX2-Positive Cell Induction Method 1

<Stage 1>

The OSR1-GFP & SIX2-tdTomato reporter human iPS cell line obtained by the method in Example 1 was cultured at 37° C. in a 2-5% $CO_2$ atmosphere to become confluent on 10-cm dishes containing a primate ES/iPS cell medium (ReproCELL) supplemented with 5 ng/ml bFGF (Wako) with the use of SNL cells (McMahon, A. P. and Bradley, A. (1990) Cell 62; 1073-1085) (the cells being treated with 15.5 μg/ml mitomycin (Kyowa Hakko Kirin Co., Ltd.) for 2 to 3 hours and seeded at a density of $3\times10^5$ cells/10-cm dish) as feeder cells. A CTK solution (2.5% Trypsin (Invitrogen), 1 mg/ml Collagenase IV (Invitrogen), 0.1 M $CaCl_2$, 10 mL KnockOut SR (Invitrogen), and 29.5 mL $H_2O$) was added to dissociate the cells. After removal of the feeder cells, the dissociated cells were suspended in a DMEM/F12 medium containing 1 μM CHIR99021 (Stemgent, 04-0004), 100 ng/ml Activin A (R&D Systems, 338-AC), 1% GlutaMAX (100×) (Invitrogen, 35050-061), 2% FBS (Hyclone), and 0.5% PenStrep (Invitrogen, 10565). Then, the cell suspensions were transferred to a low cell binding plate (LOW CELL BIND 6 WELL DISH (Nunc, 145383)) such that each well contained one-third to one-sixth of the cell suspension obtained from the 10-cm dish, followed by suspension culture at 37° C. in a 5% $CO_2$ atmosphere for 2 days.

<Stage 2>

The cell mass obtained at stage 1 was transferred to a 24-well or 6-well dish coated with Matrigel (BD Matrigel Matrix Growth Factor Reduced (BD Biosciences, 356230) (the dish being coated with 0.2 mg/ml Matrigel in DMEM and treated at 37° C. for 30 minutes or at 4° C. overnight) or a 24-well or 6-well dish coated with Synthemax (Corning Synthemax II-SC Substrate (Corning, 3535XX1)) (the dish being coated with Synthemax diluted 40-fold with sterile water and treated at room temperature for 2 hours). The medium was exchanged with a DMEM/F12 medium containing 1 µM CHIR99021, 100 ng/ml BMP7 (Recombinant human BMP7 (R&D Systems, 3534-BP)), 0.1% 2-mercaptoethanol (1000×) (Invitrogen, 21985), 1% GlutaMAX (100×), 10% KnockOut SR (Invitrogen), 0.1 mM MEM NEAA (Invitrogen, 11140), and 0.5% PenStrep, followed by adhesion culture at 37° C. in a 5% $CO_2$ atmosphere for 3 to 6 days. In the case of culture for 3 days or more, the medium was exchanged every 3 days with a medium having the same conditions.

<Stage 3>

The medium was removed from the cells obtained at stage 2. The cells were washed with PBS and then the medium was exchanged with a DMEM/F12 medium containing 5 ng/ml TGFβ1 (Peprotech, 100-21C), 0.5 µM Dorsomorphin (AMPK Inhibitor, Compound C (Merck, 171260)), 0.1% 2-mercaptoethanol (1000×), 1% GlutaMAX (100×), 10% KnockOut SR, 0.1 mM MEM NEAA, and 0.5% PenStrep, followed by suspension culture at 37° C. in a 5% $CO_2$ atmosphere for 15 to 22 days. In this case, the medium was exchanged every 3 days with a medium having the same conditions. The SIX2-tdTomato-positive cell rate for the obtained cells was determined using a flow cytometer (Becton, Dickinson and Company) for evaluation, and it was found to be 21.5±2.0% (FIG. 1B).

Example 3

SIX2-Positive Cell Induction Method 2

<Stage 1>

The OSR1-GFP & SIX2-tdTomato reporter human iPS cell line obtained by the method in Example 1 was cultured in the manner described in stage 1 of induction method 1 to become confluent on 10-cm dishes using SNL cells as feeder cells. A CTK solution was added to dissociate the cells. After removal of the feeder cells, the dissociated cells were suspended in a DMEM/F12 medium containing 1 µM TTNPB (Sigma, T3757), 1 µM CHIR99021, 1% GlutaMAX (100×), 2% FBS, and 0.5% PenStrep. Then, the cell suspensions were transferred to a low cell binding plate (LOW CELL BIND 6 WELL DISH) such that each well contained one-third to one-sixth of the cell suspension obtained from the 10-cm dish, followed by suspension culture at 37° C. in a 5% $CO_2$ atmosphere for 2 days.

<Stage 2>

The cell mass obtained at stage 1 was transferred to dishes coated with Matrigel or dishes coated with Synthemax (prepared in the manner described in stage 2 of induction method 1). The medium was exchanged with a DMEM/F12 medium containing 1 µM TTNPB, 0.1% 2-mercaptoethanol (1000×), 1% GlutaMAX (100×), 10% KnockOut SR, 0.1 mM MEM NEAA, and 0.5% PenStrep, followed by adhesion culture at 37° C. in a 5% $CO_2$ atmosphere for 3 to 9 days. In this case, the medium was exchanged every 3 days with a medium having the same conditions.

<Stage 3>

The medium was removed from the cells obtained at stage 2. The cells were washed with PBS and then the medium was exchanged with a DMEM/F12 medium containing 5 ng/ml TGFβ1, 0.5 µM Dorsomorphin, 0.1% 2-mercaptoethanol (1000×), 1% GlutaMAX (100×), 10% KnockOut SR, 0.1 mM MEM NEAA, and 0.5% PenStrep, followed by suspension culture at 37° C. in a 5% $CO_2$ atmosphere for 12 to 22 days. In this case, the medium was exchanged every 3 days with a medium having the same conditions. The SIX2-tdTomato-positive cell rate in the obtained cells was determined using a flow cytometer for evaluation, and it was found to be 20.6±5.3% (FIG. 1C).

Example 4

SIX2-Positive Cell Induction Method 3

<Stage 1>

The OSR1-GFP & SIX2-tdTomato reporter human iPS cell line obtained by the method in Example 1 was cultured in the manner described in stage 1 of induction method 1 to become confluent in 10-cm dishes using SNL cells as feeder cells. A CTK solution was added to dissociate the cells. After removal of the feeder cells, Accutase™ (Innovative Cell Technologies, AT-104) was added to disperse iPS cells to result in single cells. Then, the obtained cells were suspended in a DMEM/F12 medium containing 10 µM Y-27632 (Wako, 253-00513), 1 µM CHIR99021, 1 µM TTNPB, 1% GlutaMAX (100×), 2% FBS, and 0.5% PenStrep. The obtained cell suspensions ($1 \times 10^5$ cells/well (for a 96-well dish)) were transferred to a dish coated with 0.1% gelatin (Gelatin from porcine skin, Type A (Sigma, G1890)), followed by adhesion culture at 37° C. in a 5% $CO_2$ atmosphere for 2 days.

<Stage 2>

The cells obtained at stage 1 were washed with PBS. The medium was exchanged with a DMEM/F12 medium containing 1 µM TTNPB, 0.1% 2-mercaptoethanol (1000×), 1% GlutaMAX (100×), 10% KnockOut SR, 0.1 mM MEM NEAA, and 0.5% PenStrep, followed by adhesion culture at 37° C. in a 5% $CO_2$ atmosphere for 3 to 9 days. In this case, the medium was exchanged every 3 days with a medium having the same conditions.

<Stage 3>

Accutase™ was added to cells obtained at stage 2 to dissociate the cells. OSR1-positive cells were sorted by FACS using the expression of OSR1 (GFP) as an indicator. The obtained OSR1-positive cells were transferred to a low cell binding plate (LOW CELL BIND 6WELL DISH) at $1 \times 10^6$ cells/well in a DMEM/F12 medium containing 5 ng/ml TGFβ1, 0.5 µM Dorsomorphin, 0.1% 2-mercaptoethanol (1000×), 1% GlutaMAX (100×), 10% KnockOut SR, 0.1 mM MEM NEAA, and 0.5% PenStrep, followed by suspension culture at 37° C. in a 5% $CO_2$ atmosphere for 2 days. The obtained cell mass was transferred to dishes coated with Matrigel (BD Matrigel Matrix Growth Factor Reduced), and subsequently subjected to adhesion culture in a DMEM/F12 medium containing 5 ng/ml TGFβ1, 0.5 µM Dorsomorphin, 0.1% 2-mercaptoethanol (1000×), 1% GlutaMAX (100×), 10% KnockOut SR, 0.1 mM MEM NEAA, and 0.5% PenStrep, at 37° C. in a 5% $CO_2$ atmosphere for 2 to 13 days. In this case, the medium was exchanged every 3 days with a medium having the same conditions. The SIX2-tdTomato-positive cell rate in the obtained cells was determined using a flow cytometer for evaluation, and it was found to be 31.1±10.0% (FIG. 1D).

Example 5

Examination Using Alternatives for Dorsomorphin

Figure 2:
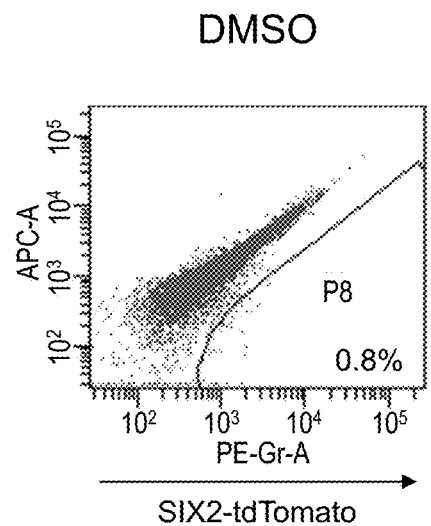
FIG. 2, including
Figure 2:
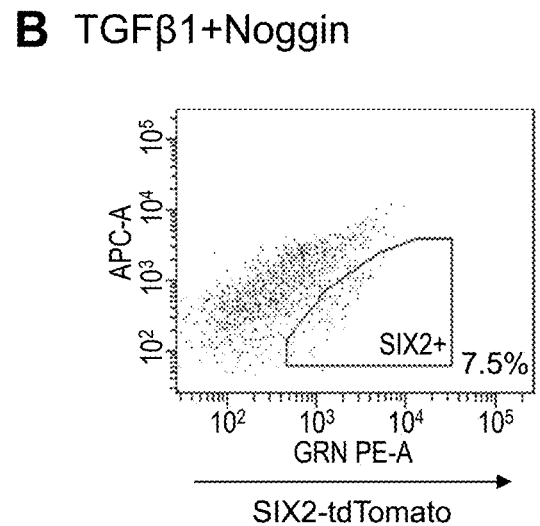
Figure 2:
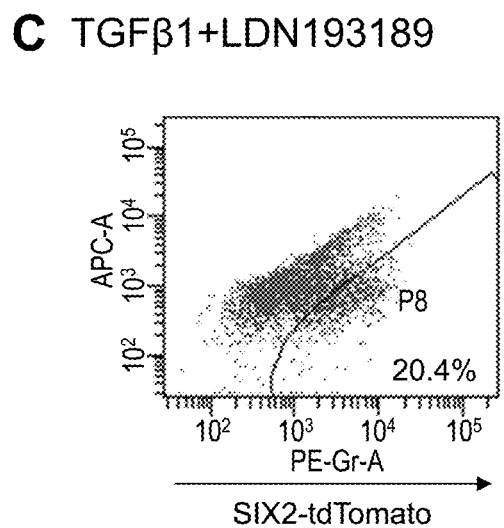
Figure 2:
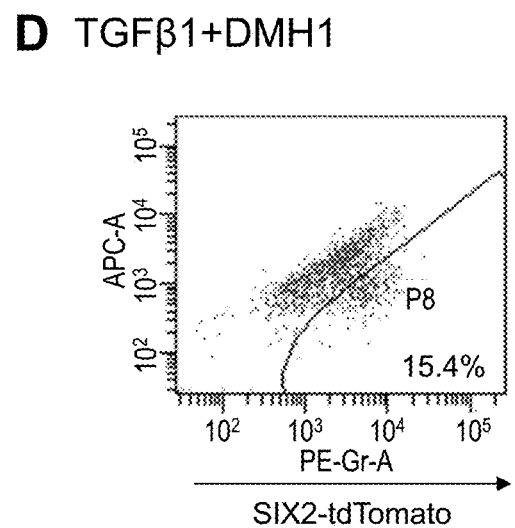
Figure 2:
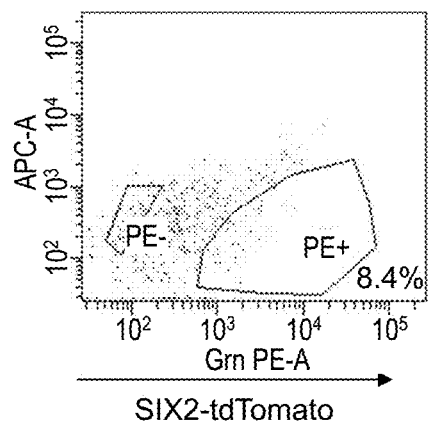
Figure 2:
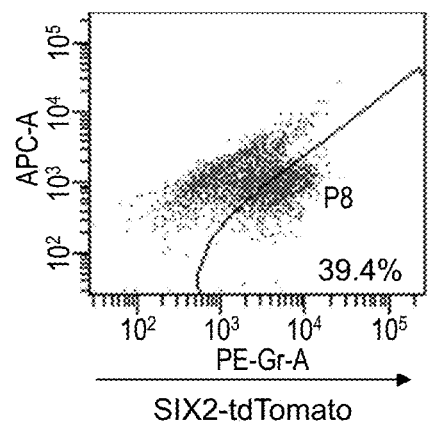
Figure 2:
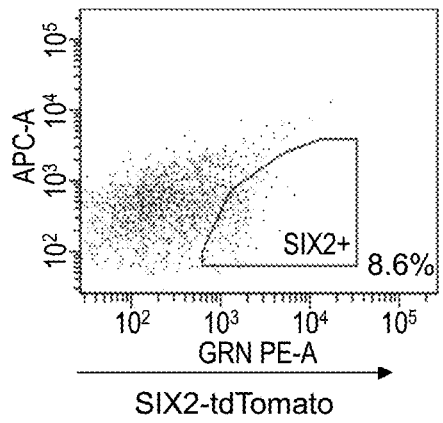
Figure 2:
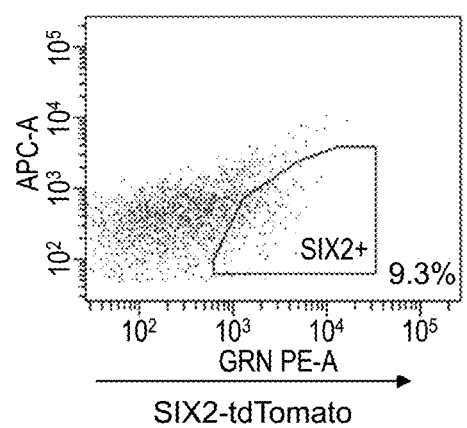

At stage 3 of SIX2-positive cell induction method 1, Dorsomorphin was replaced with 100 ng/ml Noggin (Peprotech), 0.5 µM LDN193189 (Axon MedChem, 1509), or 0.5 µM DMH1 (Tocris, 4126) for differentiation induction in the aforementioned manner. As a result, the SIX2-tdTomato-positive cell rates were found to be 7.5%, 20.4%, and 15.4%, respectively (FIGS. 2B, 2C and 2D, respectively).
[Examination Using Alternatives for TGFβ1]
At stage 3 of SIX2-positive cell induction method 1, TGFβ1 was exchanged with 50 µM IDE1 (Tocris) or 50 µM IDE2 (Tocris) for differentiation induction in the aforementioned manner. As a result, the SIX2-tdTomato-positive cell rates were 8.4% and 39.4%, respectively (FIGS. 2E and 2F).
[Examination Using a Combination of Alternatives]
At stage 3 of SIX2-positive cell induction method 1, Dorsomorphin was replaced with 0.5 µM LDN193189, while TGFβ1 with 10 ng/ml TGFβ2 (Peprotech) or 10 ng/ml TGFβ3 (R&D), for differentiation induction in the aforementioned manner. As a result, the SIX2-positive cell rates were 8.6% and 9.3%, respectively (FIGS. 2G and 2H).

Example 6

Establishment of OSR1-GFP & SIX2-tdTomato Knock-In Human iPS Cell Line

An OSR1-GFP & SIX2-tdTomato reporter human iPS cell line (4A6C3-10) was prepared from the OSR1-GFP reporter human iPS cell line (3D45) described in Mae S, et al, Nat Commun. 4: 1367, 2013 using a method similar to that in Example 1.

Example 7

SIX2-Positive Cell Induction Method 4

Figure 3:
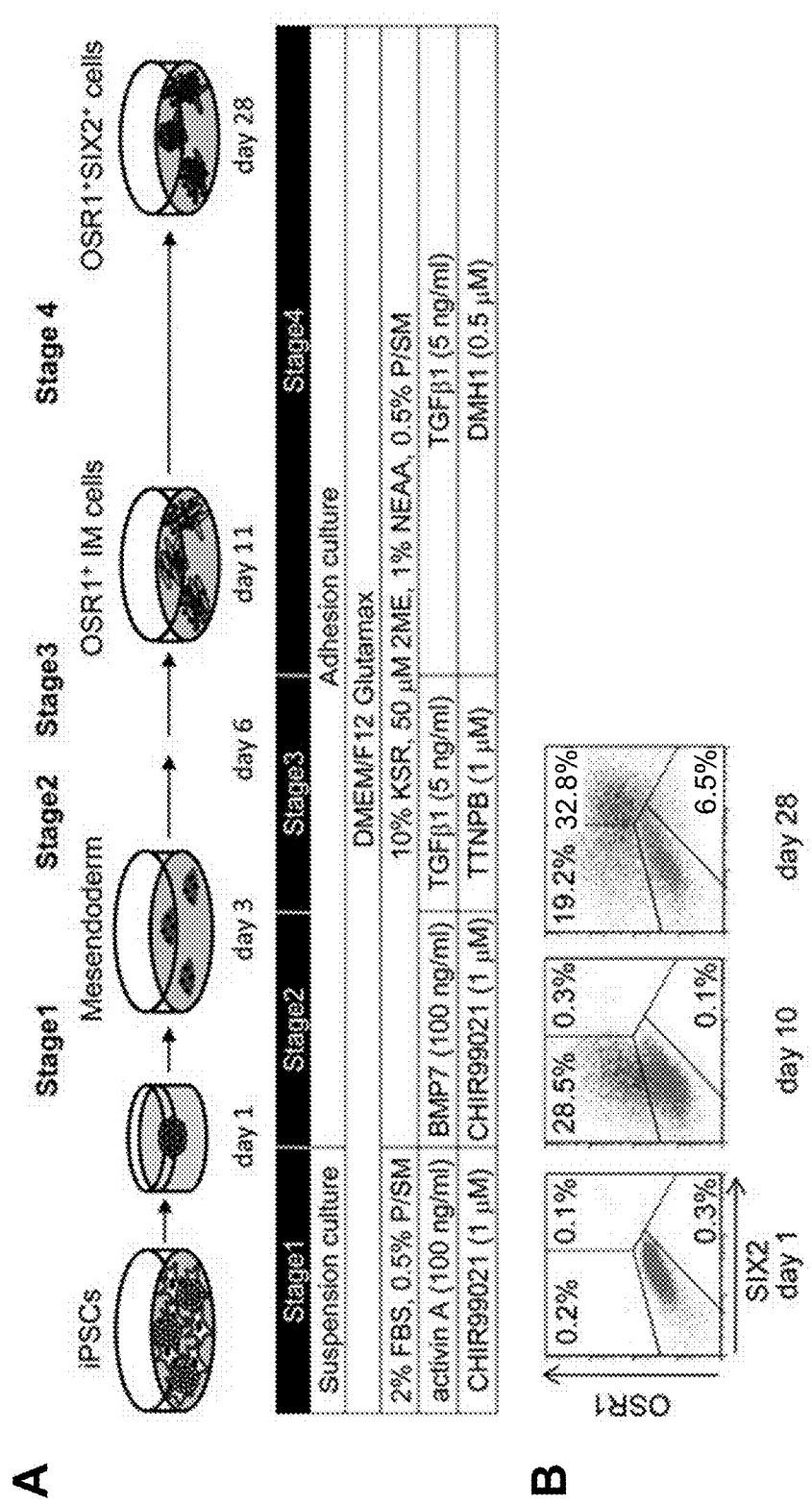
FIG. 3, including
Figure 3:
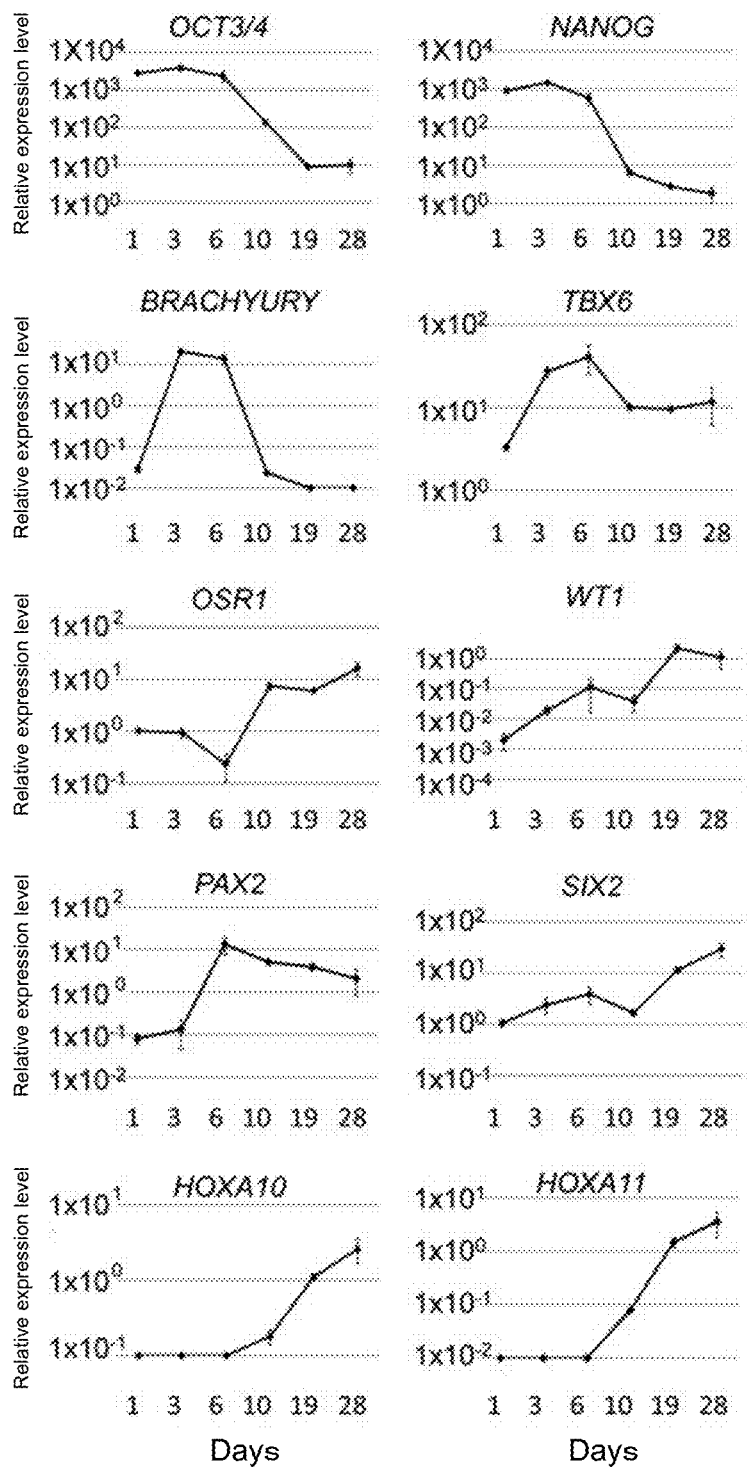
Figure 3:
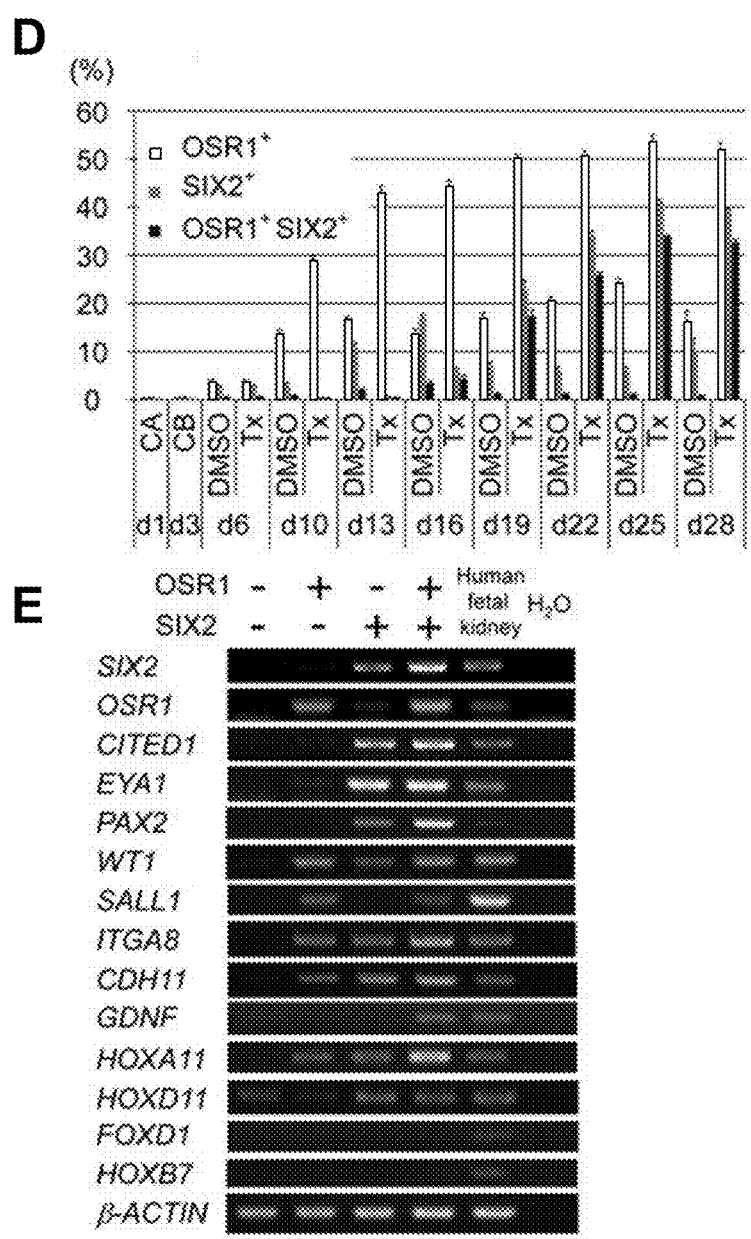

<Stage 1>
An OSR1-GFP & SIX2-tdTomato Reporter Human iPS Cell Line Obtained by the Method Described in Example 6
4A6C3-10 was cultured at 37° C. in a 2% to 5% $CO_2$ atmosphere to become 70% to 80% confluent on 10-cm dishes containing a primate ES medium (ReproCELL) supplemented with 500 U/ml penicillin/streptomycin (Invitrogen) and 5 ng/ml recombinant human basic fibroblast growth factor (bFGF, Wako) with the use of ICR-mouse-embryo (fetus 12.5 days old)-derived mouse embryonic fibroblasts (MEF) or SNL feeder cells (McMahon, A. P. and Bradley, A. (1990) Cell 62; 1073-1085) (these cells being previously treated with 15.5 µg/ml mitomycin (Kyowa Hakko Kirin Co., Ltd.) for 2 to 3 hours and seeded at a density of $2×10^5$ cells/6-cm dish) as feeder cells. The 10-cm plates containing the cells were rinsed with PBS and treated with a CTK solution (PBS containing 0.25% Trypsin (Invitrogen), 0.1% Collagenase IV (Invitrogen), 20% KnockOut SR (KSR, Invitrogen), and 1 mM $CaCl_2$) at 37° C. for 4 minutes. The CTK solution was removed by rinsing with PBS. Then, the medium was exchanged with DMEM/F12+Glutamax (Invitrogen) containing 0.1 mM MEM NEAA (Invitrogen), 1000 U/ml penicillin/streptomycin, 0.55 mM 2-mercaptoethanol (Invitrogen), and 20% KSR. Subsequently, the cells were scraped using a cell scraper and seeded on 6-cm plates coated with 0.2% gelatin to remove feeder cells. One hour later, the cells were washed with DMEM/F12+Glutamax [stage-1 medium] containing 500 U/ml penicillin/streptomycin and 2% FBS (HyClone), transferred to ultra-low attachment dishes (Corning 3471) having a stage-1 medium containing 100 ng/ml recombinant human/mouse/rat Activin A (R&D Systems) and 1 µM CHIR99021, and cultured at 37° C. in a 5% $CO_2$ atmosphere for 2 days.
<Stage 2>
In order to differentiate into the intermediate mesoderm, the cell mass (embryoid body (EB)) obtained at stage 1 was transferred to a 24-well plate coated with Synthemax II (Corning), the medium was exchanged with DMEM/F12+Glutamax containing 0.1 mM MEM NEAA, 500 U/ml penicillin/streptomycin, 0.55 mM 2-mercaptoethanol, 10% KSR, 100 ng/ml BMP7 (recombinant human BMP7, R&D Systems), and 1 µM CHIR99021, and the cells were cultured at 37° C. in a 5% $CO_2$ atmosphere for 3 days.
<Stage 3>
After stage 2, the medium was exchanged with DMEM/F12+Glutamax containing 0.1 mM MEM NEAA, 500 U/ml penicillin/streptomycin, 0.55 mM 2-mercaptoethanol, 10% KSR, 1 µM TTNPB (Sigma T3757), and 5 ng/ml TGFβ1 (Peprotech), followed by culturing at 37° C. in a 5% $CO_2$ atmosphere for 5 days. The medium was exchanged with a medium having the same conditions two days after the start of culture (i.e., day 8 from the start of stage 1 (day 1)).
<Stage 4>
After stage 3, the medium was exchanged with DMEM/F12+Glutamax containing 0.1 mM MEM NEAA, 500 U/ml penicillin/streptomycin, 0.55 mM 2-mercaptoethanol, 10% KSR, 5 ng/ml TGFβ1, and 0.5 µM DMH1 (Tocris), followed by culturing at 37° C. in a 5% $CO_2$ atmosphere for 17 days (i.e., culturing for 28 days in total from the start of stage 1 (day 1); FIG. 3A). In this case, the medium was exchanged every 3 days with a medium having the same conditions. The OSR1-positive and SIX2-positive ($OSR1^+SIX2^+$) cell rate in the obtained cells was determined using a flow cytometer for evaluation, and it was found to be 32.8% on day 28 of culture (FIG. 3B). In addition, the $OSR1^+SIX2^+$ cell rate reached the maximum level on day 25 of culture and then it was confirmed to be maintained until day 28 of culture (FIG. 3D).

Example 8

Examination Using Different Combinations of TGFβ Signaling Activators and BMP Inhibitors Induction of $OSR1^+SIX2^+$ cells from the 4A6C3-10 iPS cell line was examined using different combinations of TGFβ signaling activators and BMP inhibitors. Specifically, induction of $OSR1^+SIX2^+$ cells from 4A6C3-10 was examined under conditions 1) to 10) described below.
At stages 1 to 2 under conditions 1) to 10), the methods used at stages 1 to 2 of Example 7 were used, respectively. At stage 3 under conditions 1) to 7) and 10), the method used at stage 3 of Example 7 was used. At stage 3 under condition 8), culture was performed in the same medium as that in stage 3 of Example 7 except that 5 ng/ml TGFβ1 and 1 µM TTNPB were replaced with 5 ng/ml TGFβ2 (Peprotech). At stage 3 under condition 9), culture was performed in the same medium as that in stage 3 of Example 7 except that 5 ng/ml TGFβ1 and 1 µM TTNPB were replaced with 5 ng/ml TGFβ3 (Peprotech). At stage 4 under conditions 1) to 10), culture was performed by the method used at stage 4 of Example 7, or was performed in the same medium as in stage 4 of Example 7 except that 5 ng/ml TGFβ1 and 0.5μM DMH1 were replaced with the following: condition 1), DMSO alone; condition 2), 5 ng/ml TGFβ1; condition 3), 0.5 μM DMH1; condition 4), 5 ng/ml TGFβ1 and 100 ng/ml Noggin (Peprotech); condition 5), 5 ng/ml TGFβ1 and 0.5 μM Dorsomorphin (Merck); condition 6), 5 ng/ml TGFβ1 and 0.5 μM LDN193189 (Axon MedChem); condition 7), 5 ng/ml TGFβ1 (Peprotech) and 0.5 μM DMH1 (as in Example 7); condition 8), 5 ng/ml TGFβ2 (Peprotech) and 0.5 μM DMH1; condition 9), 5 ng/ml TGFβ3 (Peprotech) and 0.5 μM DMH1; and condition 10), 50 μM IDE2 (Tocris) and 0.5 μM DMH1.

Figure 4:
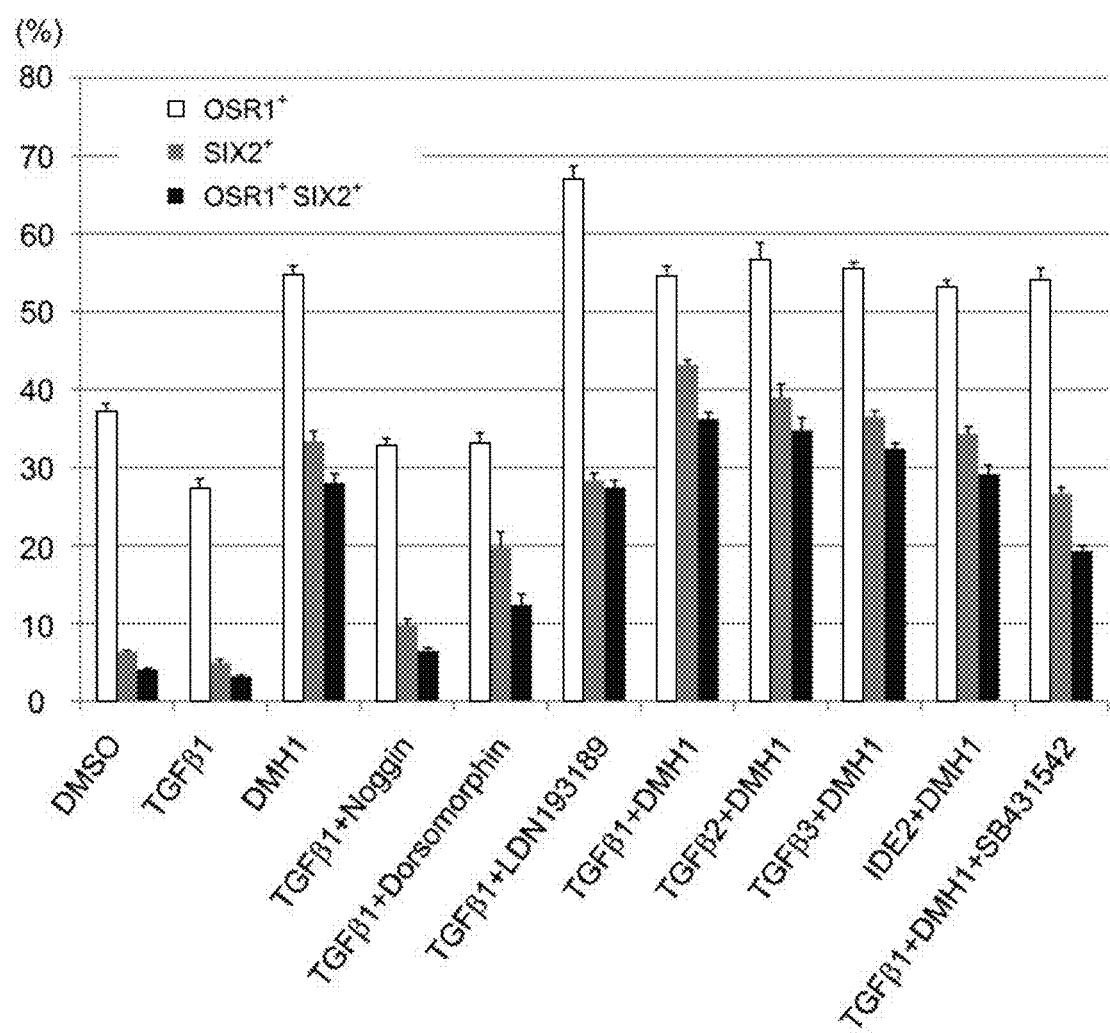
FIG. 4 shows the effects of each combination of TGFβ signaling activators and BMP inhibitors on induction of OSR1$^+$SIX2$^+$ cells from human iPS cells. Data are expressed as mean±S.E.M (n=5).

As a result, (as shown in FIG. 4), it is confirmed that using TGFβ1 as TGFβ signaling activator and DMH1 as BMP inhibitor is effective for induction of OSR1$^+$SIX2$^+$ cells. At stage 4 of Example 7, when culture was performed in a medium containing SB431542 (Tocris) (10 μM), a TGFβ receptor 1 inhibitor, together with 5 ng/ml TGFβ1 and 0.5 μM DMH1 (condition 11), differentiation into OSR1$^+$SIX2$^+$ cells was inhibited.

Example 9

Investigation with the Use of Different Human iPS Cells and Human ES Cells

Figure 5:
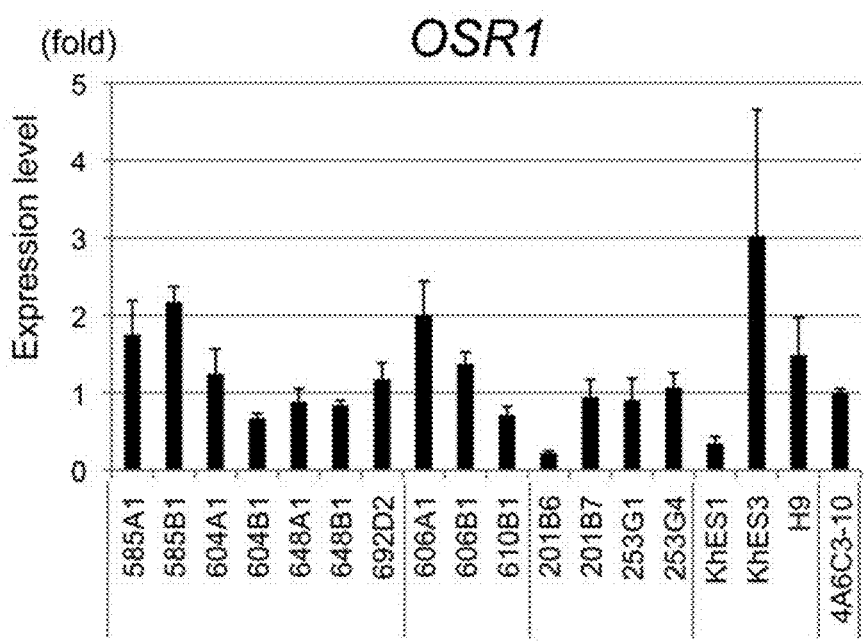
FIG. 5, including
Figure 5:
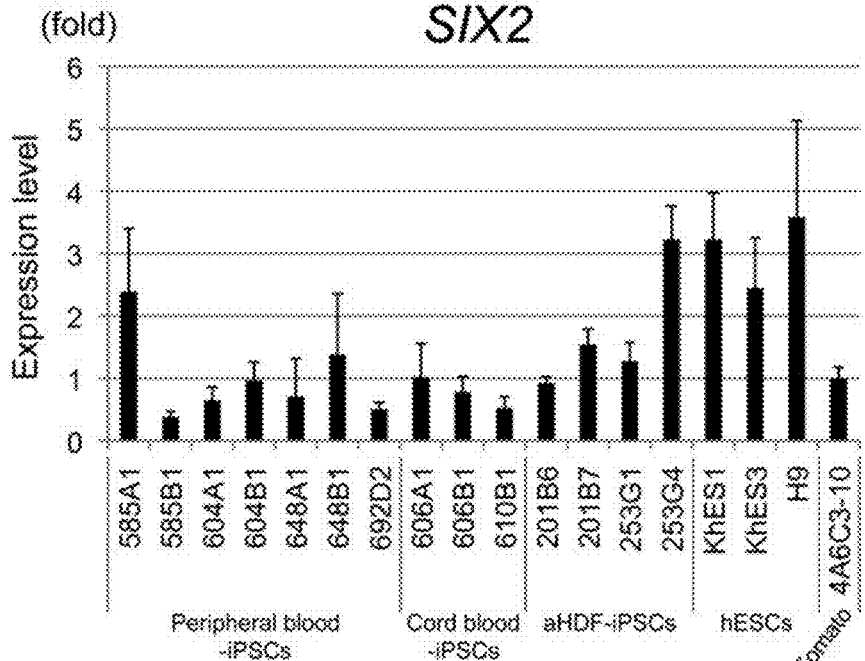

Fifteen types of human iPS cells (peripheral-blood-derived iPS cells 585A1, 585B1, 604A1, 604B1, 648A1, 648B1, and 692D2; umbilical-cord-blood-derived iPS cells 606A1, 606B1, and 610B1; adult human dermal fibroblast (aHDF)-derived iPS cells 201B6, 201B7, 253G1, and 253G4; and 4A6C3-10) and three types of human ES cells (khES1, khES3, and H9) (Proc Natl Acad Sci USA 109, 12538-12543 (2012), Stem Cells 31, 458-466 (2013)) were treated by the method described in Example 7 and were then analyzed for gene expression of OSR1 and SIX2 using quantitative RT-PCR (Nat Commun 4, 1367, (2013)). Expression of OSR1 and SIX2 in a plurality of cell lines other than 4A6C3-10 was confirmed by the method described in Example 7 (FIG. 5). Thus, it was confirmed that the method could be applied to other iPS cells and ES cells.

Example 10

Analysis of Expression Markers

Various expression markers in 4A6C3-10 treated in the induction step of Example 7 were analyzed using RT-PCR or quantitative RT-PCR. FIGS. 3C and 3E show the results. Expression of BRACHYURY and TBX6 serving as markers for the early posterior nascent mesoderm was confirmed in cells after stage 1, and expression of OSR1 serving as an intermediate mesoderm marker was confirmed in cells after stage 2 (FIG. 3C). Then, expression of WT1, PAX2, SIX2, and posterior HOX genes serving as metanephric mesenchymal markers was activated (FIG. 3C). Expression of CITED1, EYA1, PAX2, WT1, SALL1, ITGA8, CDH11, GDNF, HOXA11, and HOXD11 serving as renal progenitor cell markers was confirmed in OSR1$^+$SIX2$^+$ cells on day 28 of culture. In contrast, FOXD1 serving as a stromal marker, and HOXB7 serving as a mesonephric duct and ureteric bud marker were not detected in the cells (FIG. 3E).
[Evaluation of Renal Progenitor Cells]

Figure 6:
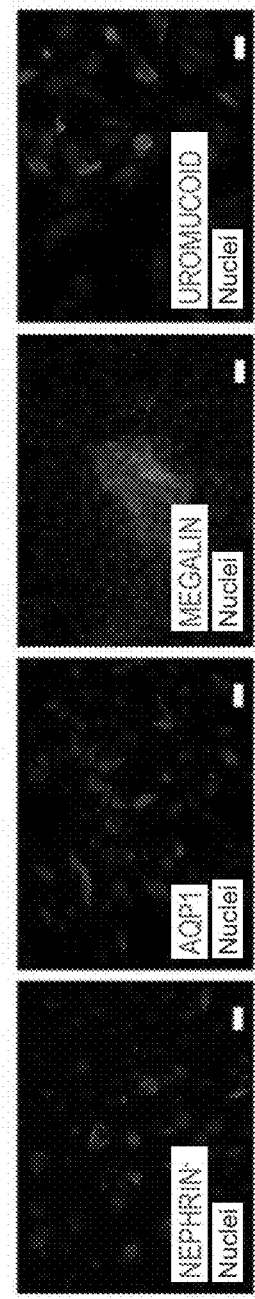
FIG. 6, including
Figure 6:
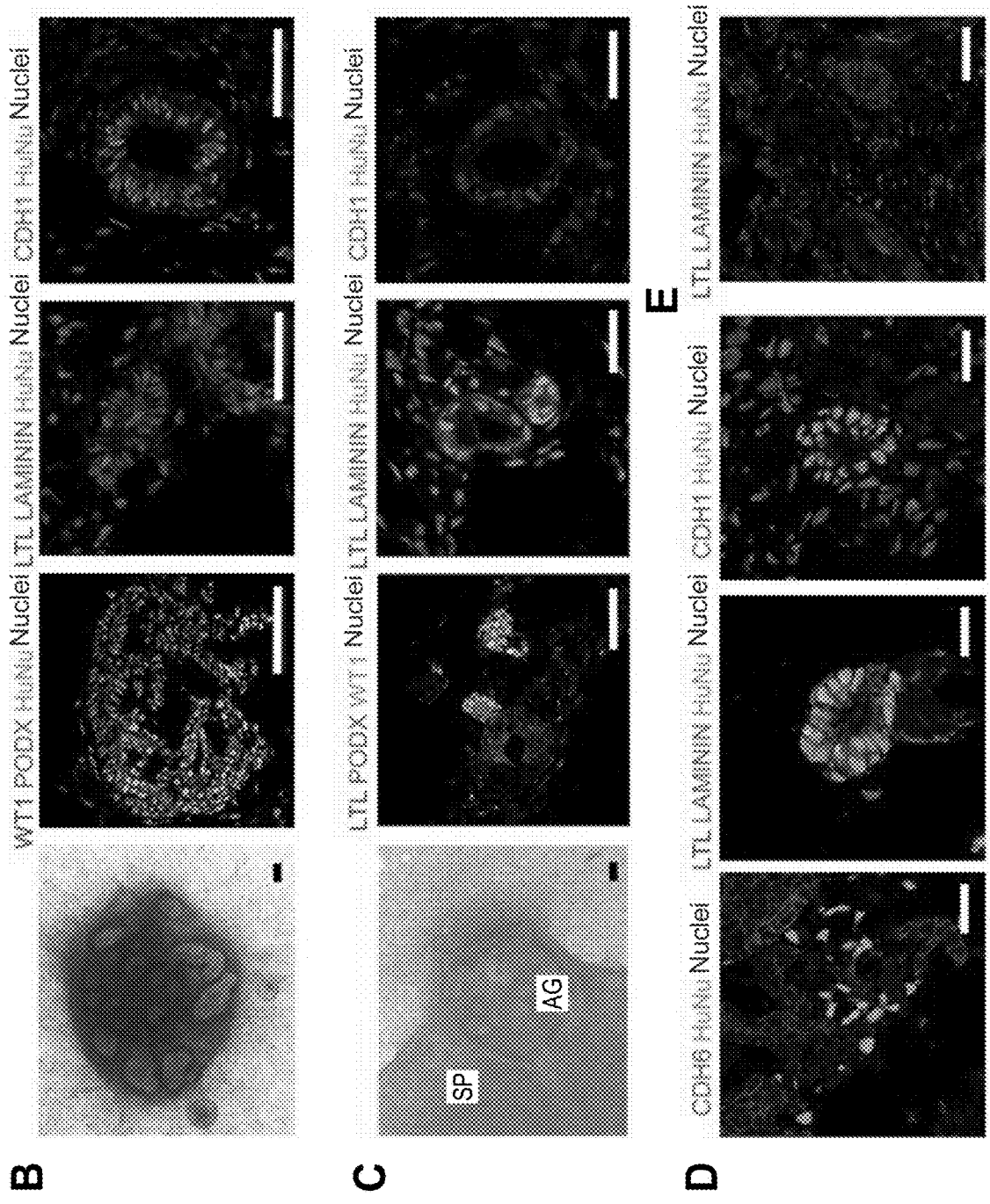
Figure 6:
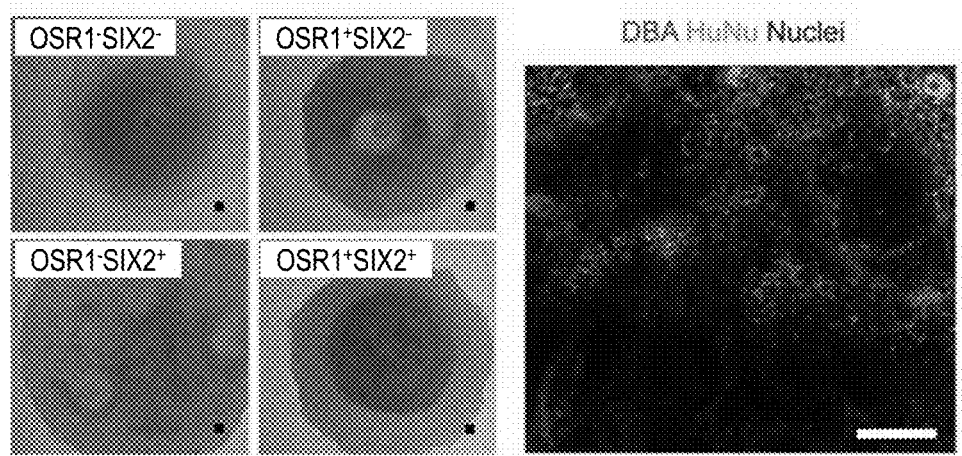

OSR1$^+$SIX2$^+$ cells on day 28 of culture treated in the induction step of Example 7 were isolated by flow cytometry, seeded on a 96-well plate coated with Synthemax II at a density of 3.0×10$^4$ cells/well, and cultured in an REGM medium (LONZA) supplemented with 10 μM Y-27632 at 37° C. in a 5% CO$_2$ atmosphere for 7 days. The obtained cells were subjected to immunostaining against NEPHRIN (a glomerular podocytes marker), AQP1 and MEGALIN (proximal tubule markers), and UROMUCOID (a Henle's loop marker) to confirm cells positive for each marker (FIG. 6A).

Subsequently, the OSR1$^+$SIX2$^+$ cells were seeded on a spindle-shaped bottom low-adhesion 96-well plate (Lipidure Coat, NOF) containing a UBC culture supernatant (see below) supplemented with 50 ng/ml BMP7 (R&D Systems) and 10 μM Y-27632 (Wako) at a density of 1.0×10$^5$ cells/well and cultured at 37° C. in a 5% CO$_2$ atmosphere for 24 hours. Next, the medium was exchanged with a UBC culture supernatant supplemented with 50 ng/ml BMP7, 0.5 μM BIO (Wako), and 10 μM Y-27632, followed by culturing for 2 to 3 days. Then, cells were recovered, seeded on mitomycin-treated NIH3T3 capable of expressing Wnt4 (Osafune K, et al. (2006), Development 133: 151-61) at a density of 3.0×10$^4$ cells/well (24-well plate), and cultured for 5 to 7 days. The obtained cells were subjected to immunostaining against Lotus Tetragonolobus lectin (LTL) (a proximal tubule marker), LAMININ (a polarized epithelium cell marker), CDH1 (a distal tubule marker), and PODOCALYXIN and WT1 (glomerular podocytes markers) to confirm cells positive for each marker (FIG. 6B).

Further, OSR1$^+$SIX2$^+$ cells were subjected to organ culture together with an E11.5 mouse embryonic spinal cord. Specifically, OSR1$^+$SIX2$^+$ cells were seeded on a spindle-shaped bottom low-adhesion 96-well plate (Lipidure Coat, NOF) containing a UBC culture supernatant (see below) supplemented with 50 ng/ml BMP7 (R&D Systems) and 10 μM Y-27632 (Wako) at a density of 1.0×10$^5$ cells/well and cultured at 37° C. in a 5% CO$_2$ atmosphere for 24 hours. Subsequently, the medium was exchanged with a UBC culture supernatant supplemented with 50 ng/ml BMP7, 0.5 μM BIO (Wako), and 10 μM Y-27632, followed by culture for 2 to 3 days. Thereafter, cells were recovered and cultured with an E11.5 mouse embryonic spinal cord at the boundary between air and a culture solution on a polycarbonate filter (Millipore) having 0.4-μm pores at 37° C. DMEM (Nacalai Tesque) supplemented with 500 U/ml penicillin/streptomycin and 10% FBS was applied to the culture solution side (Osafune K, et al. (2006), Development 133: 151-61). One week later, the obtained cells were subjected to immunostaining against LTL, LAMININ, CDH1, PODOCALYXIN, and WT1 to confirm cells positive for each marker (FIG. 6C).

Similarly, OSR1$^+$SIX2$^+$ cells were subjected to organ culture together with E11.5 mouse embryonic metanephros. Specifically, OSR1$^+$SIX2$^+$ cells were seeded on a spindle-shaped bottom low-adhesion 96-well plate (Lipidure Coat, NOF) containing a UBC culture supernatant (see below) supplemented with 50 ng/ml BMP7 (R&D Systems) and 10 μM Y-27632 (Wako) at a density of 1.0×10$^5$ cells/well and cultured at 37° C. in a 5% CO$_2$ atmosphere for 24 hours. Subsequently, the medium was exchanged with a UBC culture supernatant supplemented with 50 ng/ml BMP7, 0.5 μM BIO (Wako), and 10 μM Y-27632, followed by culturing for 2 to 3 days. Then, cells were recovered and dissociated using Accumax. The E11.5 mouse embryonic metanephros was obtained from ICR mice, cut in DMEM, left in 0.05% Trypsin-EDTA for 10 minutes, and dissociated by pipetting.

The thus separated mouse embryonic metanephric cells were allowed to stand still in DMEM supplemented with 500 U/ml penicillin/streptomycin and 10% FBS at 37° C. for 10 minutes and filtered through a 40-μm cell strainer (BD). The obtained mouse embryonic metanephric cells ($5.0 \times 10^5$ cells) were mixed with the above OSR1$^+$SIX2$^+$ cells ($5.0 \times 10^5$ cells) dissociated using Accumax. The mixed cells were cultured one whole day and night on a spindle-shaped bottom low-adhesion 96-well plate in DMEM supplemented with 10 μM Y-27632, 500 U/ml penicillin/streptomycin, and 10% FBS so as to form aggregates. The obtained aggregates were cultured at the air-fluid interface on a polycarbonate filter (Millipore) having 0.4-μm pores at 37° C. DMEM (Nacalai Tesque) supplemented with 500 U/ml penicillin/streptomycin and 10% FBS was applied to the culture solution side (Uchino, S. et al. JAMA 294, 813-818 (2005)). One week later, the obtained cells were subjected to immunostaining against CDH6 (a renal vesicle marker), LTL, LAMININ, CDH1, PODOCALYXIN, and WT1 to confirm cells positive for each marker (FIG. 6D).

Further, OSR1$^+$SIX2$^+$ cells were seeded at a density of $1.0 \times 10^5$ cells/well on a spindle-shaped bottom low-adhesion 96-well plate (Lipidure Coat, NOF) containing a UBC culture supernatant (see below) supplemented with 50 ng/ml BMP7 (R&D Systems) and 10 μM Y-27632 (Wako) and cultured at 37° C. in a 5% $CO_2$ atmosphere. Subsequently, the medium was exchanged with a UBC culture supernatant supplemented with 50 ng/ml BMP7, 0.5 μM BIO (Wako), and 10 μM Y-27632, followed by culturing for 2 to 3 days. Then, cells were recovered and transplanted into epididymal fat pads of immunodeficient mice (NOD. CB17-Prkdc$^{scid}$/J (Charles river)). Thirty days later, tissues at the transplantation sites were collected. As a result, an LTL- and LAMININ-positive proximal tubule-like structure was observed (FIG. 6E).

Further, cells of each fraction on day 28 of culture (OSR1$^-$SIX2$^-$, OSR1$^+$SIX2$^-$, OSR1$^-$SIX2$^+$, and OSR1$^+$SIX2$^+$) treated in the induction step of Example 7 were subjected to organ culture together with an E11.5 mouse embryonic ureteric bud. Specifically, iPSC-derived cells were seeded at a density of $1.0 \times 10^5$ cells/well on a spindle-shaped bottom low-adhesion 96-well plate (Lipidure Coat, NOF) containing a UBC culture supernatant (see below) supplemented with 50 ng/ml BMP7 (R&D Systems) and 10 μM Y-27632 (Wako) and cultured at 37° C. in a 5% $CO_2$ atmosphere for 24 hours. Subsequently, the medium was exchanged with a UBC culture supernatant supplemented with 50 ng/ml BMP7, 0.5 μM BIO (Wako), and 10 μM Y-27632, followed by culturing for 2 to 3 days. Then, the cells were recovered and dissociated using Accumax. An E11.5 mouse embryonic ureteric bud was obtained from an ICR mouse. Cells of the obtained mouse embryonic ureteric bud ($5.0 \times 10^5$ cells) were mixed with the cells ($5.0 \times 10^5$ cells) dissociated using Accumax of each of OSR1$^-$SIX2$^-$, OSR1$^+$SIX2$^-$, OSR1$^-$SIX2$^+$, and OSR1$^+$SIX2$^+$ cell groups. The mixed cells were cultured one whole day and night on a spindle-shaped bottom low-adhesion 96-well plate in DMEM supplemented with 10 μM Y-27632, 500 U/ml penicillin/streptomycin, and 10% FBS so as to form aggregates. The obtained aggregates were cultured at the air-fluid interface on a polycarbonate filter (Millipore) having 0.4-μm pores at 37° C. DMEM (Nacalai Tesque) supplemented with 500 U/ml penicillin/streptomycin and 10% FBS was applied to the culture solution side (Uchino, S. et al. JAMA 294, 813-818 (2005)). One week later, the obtained cell aggregates were observed and, as a result, the aggregates formed with OSR1$^+$SIX2$^+$ cells exclusively had a tubular structure (FIG. 6F, left). Further, the aggregates formed with OSR1$^+$SIX2$^+$ cells were subjected to immunostaining against DBA (a ureteric bud marker) and, as a result, mouse ureteric bud-derived branches were confirmed (FIG. 6F, right).

The above results indicated that OSR1$^+$SIX2$^+$ cells induced via differentiation by the method described in Example 7 were renal progenitor cells.

[UBC Culture Supernatant]

A ureteric-bud-cell (UBC)-conditioned medium was prepared by a modified version of the method disclosed in Am J Physiol 273, F757-767 (1997). UBC (provided by Dr. Sakurai, Proc Natl Acad Sci USA 94, 6279-6284 (1997)) was cultured in a minimum essential medium (MEM; Invitrogen) containing 10% fetal bovine serum (FBS). When cells became 80% confluent, they were rinsed with PBS, and the medium was exchanged with DMEM/F12+Glutamax containing 0.1 mM MEM NEAA, 500 U/ml penicillin/streptomycin, 0.55 mM 2-mercaptoethanol, and 10% KSR. Next, the cells were cultured for 3 days to obtain a culture supernatant. The culture supernatant was filtrated through a 0.22-μm filter before use.

Example 11

Therapeutic Effect of Human iPS-Derived Renal Progenitor Cells

Human iPS-derived renal progenitor cells (OSR1$^+$SIX2$^+$ cells; also referred to as "RP-OS") and a cell group containing human iPS-derived renal progenitor cells (OSR1$^+$SIX2$^-$ cells and OSR1$^+$SIX2$^+$ cells; also referred to as "hiPSC-RP"), which were obtained on days 25 to 28 after differentiation induction by the method described in Example 7, were isolated by flow cytometry. Each of the cells and the cell group was seeded at a density of $1.0 \times 10^5$ cells/well on a spindle-shaped bottom low-adhesion 96-well plate (Lipidure Coat, NOF) containing a UBC culture supernatant (see above) supplemented with 50 ng/ml BMP7 (R&D Systems) and 10 μM Y-27632 (Wako) and cultured at 37° C. in a 5% $CO_2$ atmosphere for 24 hours. Then, the medium was exchanged with a UBC culture supernatant supplemented with 50 ng/ml BMP7, 0.5 μM BIO (Wako), and 10 μM Y-27632, followed by culturing for 24 hours. As a control, undifferentiated human iPS cells (4A6C3-10) were seeded at a density of $1.0 \times 10^5$ cells/well on a spindle-shaped bottom low-adhesion 96-well plate containing a primate ES cell medium (ReproCELL) supplemented with 10 μM Y-27632, followed by culturing at 37° C. in a 5% $CO_2$ atmosphere for 48 hours. The cultured cells were washed with physiological saline to remove the medium. Then, as described below, 15 hiPSC-RP cell masses were transplanted under the renal subcapsules of acute kidney injury (AKI) mouse models. In addition, experiments to confirm tissue differentiation of OSR1$^+$SIX2$^+$ cells (FIGS. 7A and 7B) were carried out by injecting five RP-OS cell masses into the kidney parenchyma of an AKI mouse model or a chronic renal failure mouse model by pipetting as described below.

[Mouse Acute Kidney Injury (AM) Model Test]

A mouse ischemia-reperfusion AM model was prepared in accordance with a known method (Aging Cell 8, 192-200 (2009), J Am Soc Nephrol 20, 1544-1555 (2009), J Am Soc Nephrol 25, 316-328 (2014)). Six-week-old female immunodeficient mice (NOD. CB17-Prkdc$^{scid}$/J (Charles River)) were anesthetized by isoflurane inhalation and maintained at 37° C. A frank incision was made on each mouse to perform a right nephrectomy. Then, the left renal artery was blocked using a non-traumatic microvascular clamp (Natsume Seisakusho Co., Ltd., Japan) for 45 minutes. The clamp was removed and then RP-OS, hiPSC-RP, or 4A6C3-10 was transplanted into the mouse (and physiological saline was injected into control mice). The blood urea nitrogen (BUN) and serum creatinine (Cr) levels, which are kidney function markers in mouse peripheral blood, were determined using DRI-CHEM 7000VZ (FUJIFILM, Japan). Establishment of the AM state was confirmed with an increase in the BUN level (>41 mg/dl) after ischemia-reperfusion without renal infarction. For kidney tissue analysis, staining with Periodic acid-Schiff (PAS) or Masson's trichrome (MT) was performed on day 3 after ischemia-reperfusion (I/R).

[Mouse Chronic Renal Failure Model Test]

A mouse chronic renal failure model (5/6 nephrectomy model) was generated using a known method (Nephrol Dial Transplant 26, 832-838 (2011)). Six-week-old female immunodeficient mouse (NOD. CB17-Prkdc$^{scid}$/J) were anesthetized by isoflurane inhalation and maintained at 37° C. After right nephrectomy, the superior and inferior poles of the left kidney were excised from each mouse. Two weeks after surgery, RP-OS cell masses were transplanted into the mouse. Three days or two weeks after transplantation, the mouse was sacrificed and kidney tissue sections were tested by immunostaining.

[Results]

Figure 7:
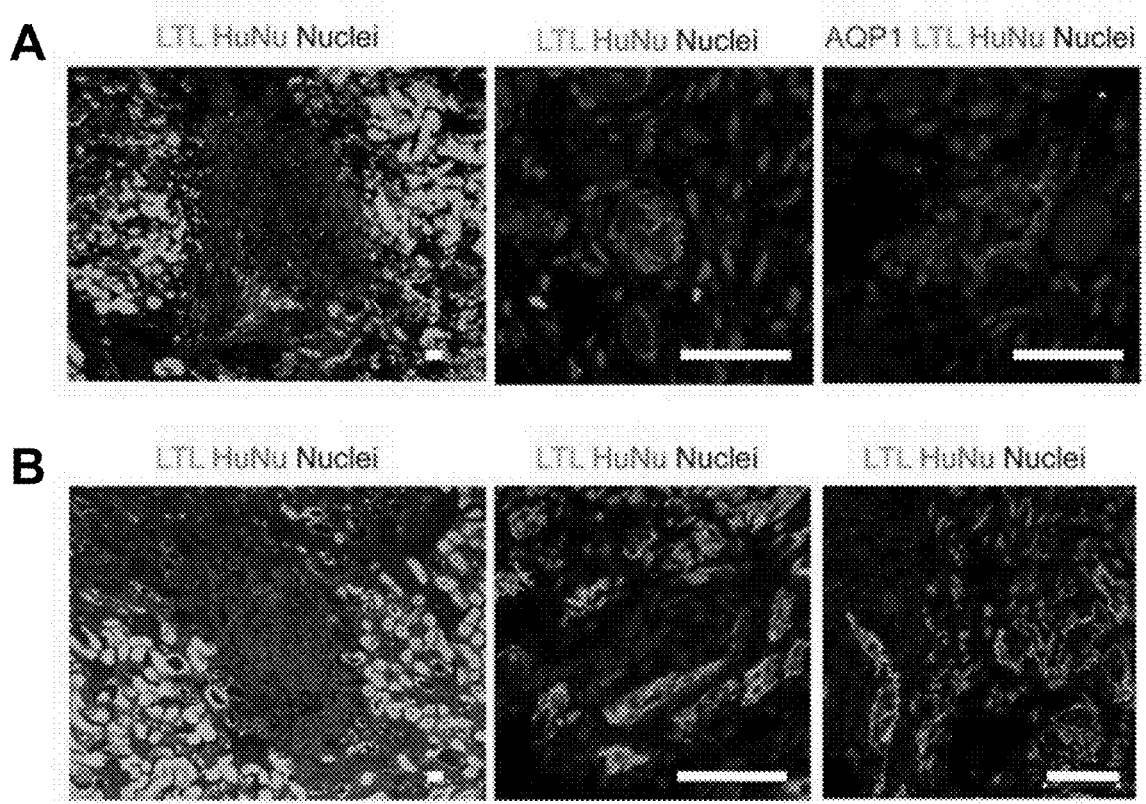
FIG. 7, including
Figure 7:
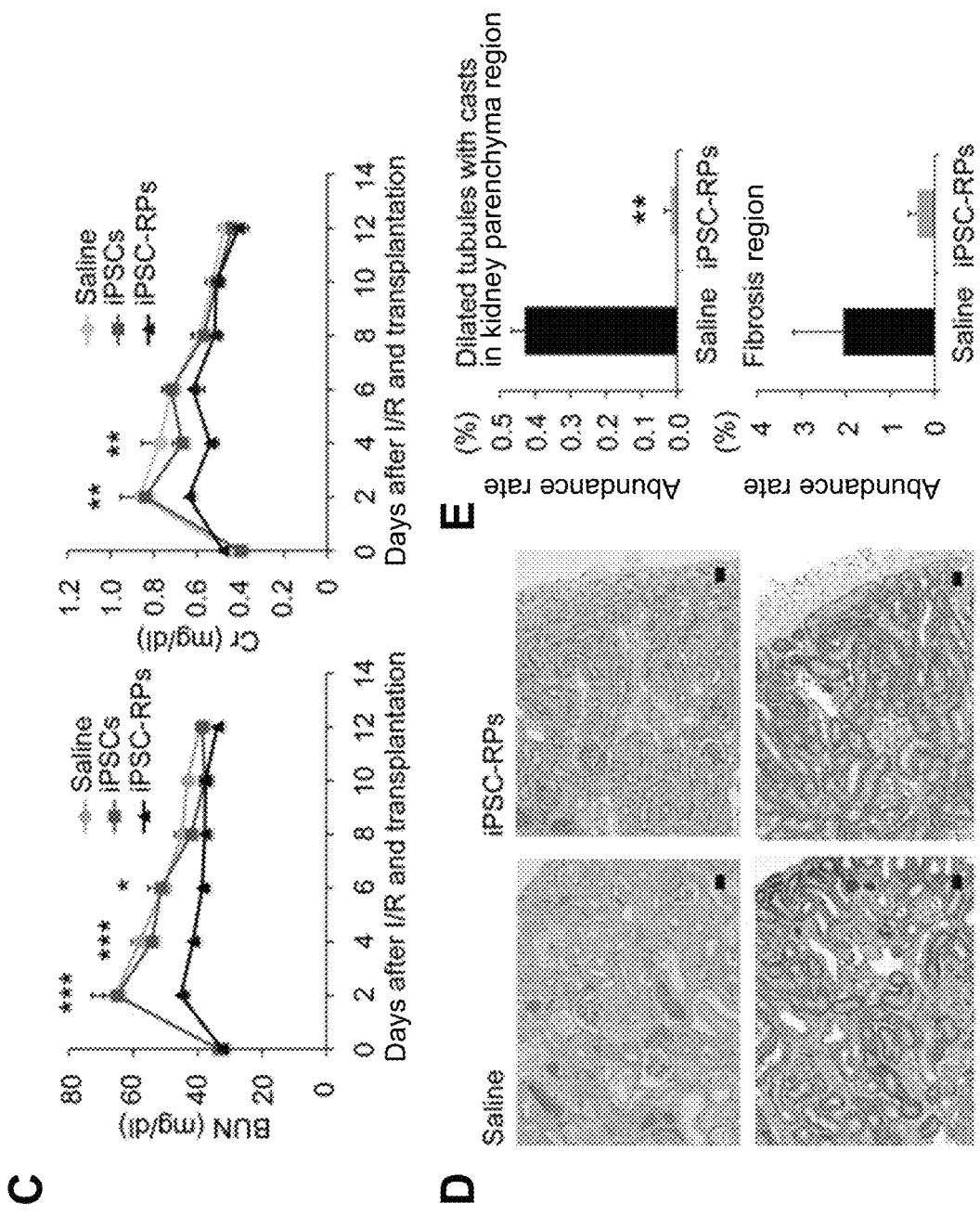

Two weeks after transplantation of RP-OS into kidney parenchyma, some of transplanted RP-OS cells were incorporated into the kidney of the host so as to differentiate into proximal tubule marker LTL- and AQP1-positive cells in both the AKI model (FIG. 7A) and the chronic renal failure model (FIG. 7B). However, as a result of transplantation of RP-OS into the kidney parenchyma, no obvious effects on kidney function were observed in either model (data not shown). Because there is a report that the renal subcapsule transplantation allows delivery of an increased number of mesenchymal stem cells directly to a damaged kidney compared with intravenous injection (Transplant Proc 41, 947-951 (2009)), we tested the therapeutic effects of the renal subcapsule transplantation of hiPSC-RP. As a result, the BUN level and the serum Cr level were found to significantly decrease in the hiPSC-RP transplantation group on days 2, 4, and 6 after ischemia-reperfusion, compared with the control group and the undifferentiated human iPS cell transplantation group (FIG. 7C). The results of histological analysis confirmed that dilated tubules with casts in the kidney parenchyma region in the hiPSC-RP transplantation group were significantly smaller than those in the control group, and the fibrosis region in the hiPSC-RP transplantation group was narrower than that in the control group (FIGS. 7D and 7E). The fact that hiPSC-RP was not incorporated into the kidney of the host suggested that therapeutic effects of hiPSC-RP confirmed through this protocol were mainly based on paracrine actions.

INDUSTRIAL APPLICABILITY

As described in detail above, the present invention provides a method for inducing differentiation of intermediate mesoderm cells into renal progenitor cells. Accordingly, renal progenitor cells produced by the method can be used for regenerative medicine for kidney diseases such as renal failure.

All publications, patents, and patent applications cited herein are incorporated herein by reference in their entirety.

The invention claimed is:

1. A method for producing renal progenitor cells from pluripotent stem cells, said method comprising:
 (i) culturing pluripotent stem cells in a medium containing one or more substances selected from the group consisting of Activin A, a GSK-3β inhibitor(s), and a retinoic acid derivative(s) for 1-3 days to obtain mesendoderm cells;
 (ii) culturing the mesendoderm cells obtained in the step (i) in a medium containing one or more substances selected from the group consisting of BMP7, a GSK-3β inhibitor(s), and a retinoic acid derivative(s) for 3 to 12 days to obtain OSR1-positive intermediate mesoderm cells; and
 (iii) culturing the intermediate mesoderm cells obtained in the step (ii) in a medium containing a TGFβ signaling activator(s) and a BMP inhibitor(s) for 2 to 20 days to generate a population of OSR1-positive, SIX2-positivere renal progenitor cells.

2. The method of claim 1, wherein the TGFβ signaling activator is one or more substances selected from the group consisting of TGFβ1, TGFβ2, TGFβ3, IDE1, and IDE2.

3. The method of claim 1, wherein the BMP inhibitor is one or more substances selected from the group consisting of Dorsomorphin, Noggin, LDN193189, and DMH1.

4. The method of claim 1, wherein the TGFβ signaling activator is TGFβ1, and the BMP inhibitor is DMH1.

5. The method of claim 1, wherein the step (ii) comprises the following steps of:
(ii-1) culturing the cells obtained in the step (i) in a medium containing one or more substances selected from BMP7 and a GSK-3β inhibitor(s); and
(ii-2) culturing the cells obtained in the step (ii-1) in a medium containing one or more substances selected from a TGFβ signaling activator(s) and a retinoic acid derivative(s).

6. The method of claim 5, wherein the step (ii-1) is a step of performing the culturing in a medium containing BMP7 and a GSK-3β inhibitor(s), and the step (ii-2) is a step of performing the culturing in a medium containing a TGFβ signaling activator(s) and a retinoic acid derivative(s).

7. The method of claim 1, wherein the GSK3β inhibitor is CHIR99021.

8. The method of claim 1, wherein the retinoic acid derivative is AM580 or TTNPB.

9. The method of claim 1, wherein the pluripotent stem cells are induced pluripotent stem (iPS) cells.

10. The method of claim 9, wherein the iPS cells are human iPS cells.

11. A method for producing renal progenitor cells, said method comprising:
(a) culturing pluripotent stem cells for 1-3 days in a medium containing one or more substances selected from the group consisting of Activin A, a GSK-3β inhibitor(s), and a retinoic acid derivative(s) to obtain mesendoderm cells; and
(b) culturing the mesendoderm cells for 3 to 12 days in a medium containing one or more substances selected from the group consisting of BMR7, a GSK-3β inhibitor(s), and a retinoic acid derivative(s) to generate a population of intermediate mesoderm cells that are OSR1-positive;
(c) culturing the intermediate mesoderm cells in a medium containing a TGFβ signaling activator(s) and a BMP inhibitor(s) for 2 to 20 days to generate a population of OSR-1 positive, SIX2-positive renal progenitor cells; and
(d) collecting OSR-1-positive, SIX2-positive renal progenitor cells from the medium of step (c).

12. The method of claim 11, wherein the TGFβ signaling activator is one or more substances selected from the group consisting of TGFβ1, TGFβ2, TGFβ3, IDE1, and IDE2.

13. The method of claim 11, wherein the BMP inhibitor is one or more substances selected from the group consisting of Dorsomorphin, Noggin, LDN193189, and DMH1.

14. The method of claim 11, wherein the TGFβ signaling activator is TGFβ1, and the BMP inhibitor is DMH1.

15. The method of claim 11, wherein the step (b) comprises the following steps of:
(b-1) culturing the cells obtained from step (a) in a medium containing one or more substances selected from BMP7 and a GSK-3β inhibitor(s); and
(b-2) culturing the cells obtained from step (b-1) in a medium containing one or more substances selected from a TGFβ signaling activator(s) and a retinoic acid derivative(s).

16. The method of claim 15, wherein the step (b-1) is a step of performing the culturing in a medium containing BMP7 and a GSK-3β inhibitor(s), and the step (b-2) is a step of performing the culturing in a medium containing a TGFβ signaling activator(s) and a retinoic acid derivative(s).

17. The method of claim 11, wherein the GSK3β inhibitor is CHIR99021.

18. The method of claim 11, wherein the retinoic acid derivative is AM580 or TTNPB.

19. The method of claim 11, wherein the pluripotent stem cells are induced pluripotent stem (iPS) cells.

* * * * *

UNITED STATES PATENT AND TRADEMARK OFFICE
CERTIFICATE OF CORRECTION

PATENT NO. : 11,225,642 B2
APPLICATION NO. : 14/897319
DATED : January 18, 2022
INVENTOR(S) : Osafune et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 805 days.

Signed and Sealed this
Twenty-fifth Day of October, 2022

Katherine Kelly Vidal
*Director of the United States Patent and Trademark Office*

SEQUENCE LISTING

```
<160> NUMBER OF SEQ ID NOS: 1

<210> SEQ ID NO 1
<211> LENGTH: 12
<212> TYPE: PRT
<213> ORGANISM: Artificial Sequence
<220> FEATURE:
<221> NAME/KEY: LIPID
<222> LOCATION: 1
<223> OTHER INFORMATION: MYRISTATE
<220> FEATURE:
<221> NAME/KEY: MOD_RES
<222> LOCATION: 11
<223> OTHER INFORMATION: PHOSPHORYLATION
<220> FEATURE:
<221> NAME/KEY: MOD_RES
<222> LOCATION: 12
<223> OTHER INFORMATION: AMIDATION

<400> SEQUENCE: 1

Gly Lys Glu Ala Pro Pro Ala Pro Pro Gln Ser Pro
1               5                   10
```